(12) United States Patent
Wu

(10) Patent No.: US 9,958,410 B2
(45) Date of Patent: May 1, 2018

(54) NORMALIZED CALIBRATION OF ANALYTE CONCENTRATION DETERMINATIONS

(71) Applicant: Bayer HealthCare LLC, Whippany, NJ (US)

(72) Inventor: Huan-Ping Wu, Granger, IN (US)

(73) Assignee: Ascensia Diabetes Care Holdings AG, Basel (CH)

( * ) Notice: Subject to any disclaimer, the term of this patent is extended or adjusted under 35 U.S.C. 154(b) by 217 days.

(21) Appl. No.: 14/774,617

(22) PCT Filed: Mar. 7, 2014

(86) PCT No.: PCT/US2014/021870
§ 371 (c)(1),
(2) Date: Sep. 10, 2015

(87) PCT Pub. No.: WO2014/159077
PCT Pub. Date: Oct. 2, 2014

(65) Prior Publication Data
US 2016/0018355 A1   Jan. 21, 2016

Related U.S. Application Data

(60) Provisional application No. 61/782,520, filed on Mar. 14, 2013.

(51) Int. Cl.
*G01N 27/327*    (2006.01)
*G06F 19/12*     (2011.01)
*G01N 33/72*     (2006.01)

(52) U.S. Cl.
CPC ....... *G01N 27/3274* (2013.01); *G01N 33/723* (2013.01); *G06F 19/12* (2013.01)

(58) Field of Classification Search
None
See application file for complete search history.

(56) References Cited

U.S. PATENT DOCUMENTS

| | | |
|---|---|---|
| 5,620,579 A | 4/1997 | Genshaw |
| 5,653,863 A | 8/1997 | Genshaw |
| 6,120,676 A | 9/2000 | Heller |
| 6,153,069 A | 11/2000 | Pottgen |
| 6,413,411 B1 | 7/2002 | Pottgen |
| 7,781,222 B2 * | 8/2010 | Wu ............... A61B 5/14532 422/82.01 |

FOREIGN PATENT DOCUMENTS

| | | |
|---|---|---|
| EP | 1 978 361 | 10/2008 |
| WO | WO 2007/013915 | 2/2007 |
| WO | WO 2007/040913 | 4/2007 |
| WO | WO 2009/108239 | 9/2009 |
| WO | WO 2010/077660 | 7/2010 |
| WO | WO 2011/119533 | 9/2011 |
| WO | WO 2011/156152 | 12/2011 |
| WO | WO 2013/043839 | 3/2013 |

OTHER PUBLICATIONS

Search Report for International Application No. PCT/US2014/021870 dated Jun. 17, 2014 (4 pages).
Written Opinion for International Application No. PCT/US2014/021870 dated Sep. 14, 2015 (6 pages).

* cited by examiner

*Primary Examiner* — Russell S Negin
(74) *Attorney, Agent, or Firm* — Nixon Peabody LLP

(57) ABSTRACT

Biosensor system measurement devices used to determine the presence and/or concentration of an analyte in a sample include normalized calibration information relating output signal or signals the device generates in response to the analyte concentration of the sample to previously determined reference sample analyte concentrations. The measurement devices use this normalized calibration information to relate one or more output signals from an electrochemical or optical analysis of a sample to the presence and/or concentration of one or more analytes in the sample. The normalized calibration information includes a normalization relationship to normalize output signals measured by the measurement device of the biosensor system and at least one normalized reference correlation relating normalized output signals to reference sample analyte concentrations.

20 Claims, 18 Drawing Sheets

100

- 110 — Measure at least two analyte responsive output signals, where the analyte responsive output signals are affected by at least one extraneous stimulus resulting from a physical characteristic, an environmental aspect, and/or a manufacturing variation error being incorporated into the analyte responsive output signal.

- 120 — Determine a reference correlation 122 by relating reference sample analyte concentrations 124 to output signals as determined by the measurement device 126.

- 130 — Measure one or more extraneous stimulus responsive output signals from the reference samples and quantify the extraneous stimulus to provide at least two quantified extraneous stimulus values 132.

- 140 — Determine a normalizing relationship 142 from the analyte responsive output signals and the at least two quantified extraneous stimulus values 132 at a single selected sample analyte concentration.

- 150 — Determine a normalizing value 152 from the normalizing relationship 142 by inputting the quantified extraneous stimulus values 132 into the normalizing relationship 142.

- 160 — Divide the analyte responsive output signals by the normalizing values 152 to provide normalized analyte responsive output signals 162.

- 170 — Determine a normalized reference correlation 172 between the normalized analyte responsive output signals 162 and the reference sample analyte concentrations 114 by a regression technique.

```
┌─────────────────────────────────────────────────────────────┐
│ Measure one or more analyte responsive output signal values 222 │──220
│ from the sample, where the analyte responsive output signals are │
│ affected by a stimulus resulting from a physical characteristic, an │
│ environmental aspect, and/or a manufacturing variation error being │
│ incorporated into the analyte responsive output signal.          │
└─────────────────────────────────────────────────────────────┘
                              │
                              ▼
┌─────────────────────────────────────────────────────────────┐
│  Measure one or more extraneous stimulus responsive output   │──230
│   signals and quantify the extraneous stimulus to provide a  │
│  quantified stimulus value for each extraneous stimulus 232, 234. │
└─────────────────────────────────────────────────────────────┘
                              │
                              ▼                                250
┌─────────────────────────────────────────────────────────────┐
│ Determine one or more normalizing values from one or more previously │
│              determined normalizing relationships.            │
└─────────────────────────────────────────────────────────────┘
                              │
                              ▼
┌─────────────────────────────────────────────────────────────┐
│  Determine at least one normalized analyte responsive output signal │──260
│  value by dividing the analyte responsive output signal values 222 by the │
│       normalizing value to determine one or more normalized analyte │
│     responsive output signal values 262 (in the case of one external │
│          stimulus) or 267 (in the case of two external stimulus).  │
└─────────────────────────────────────────────────────────────┘
                              │
                              ▼
┌─────────────────────────────────────────────────────────────┐
│   Transform the one or more normalized analyte responsive output │──280
│     signal values 262 or 267 into an analyte concentration of the │
│     sample 282 with a previously determined normalized reference │
│      correlation, such as the previously described normalized    │
│                 reference correlation 172 or 177.               │
└─────────────────────────────────────────────────────────────┘
                              │
                              ▼
┌─────────────────────────────────────────────────────────────┐
│   Display, store for future reference, compensate, and/or use for │──290
│     additional calculations the determined analyte concentration of │
│                        the sample 282.                          │
└─────────────────────────────────────────────────────────────┘
```

FIG. 1C

NORMALIZED CALIBRATION OF ANALYTE CONCENTRATION DETERMINATIONS

REFERENCE TO RELATED APPLICATIONS

This application is a U.S. national phase of International Application No. PCT/US2014/021870, filed Mar. 7, 2014, titled "Normalized Calibration Of Analyte Concentration Determinations," which claims the benefit of priority of U.S. Provisional Patent Application No. 61/782,520, filed Mar. 14, 2013, titled "Calibration Of Analyte Concentration Determinations," each of which are incorporated by reference in their entirety.

BACKGROUND

Biosensor systems provide an analysis of a biological fluid sample, such as blood, serum, plasma, urine, saliva, interstitial, or intracellular fluid. Typically, the systems include a measurement device that analyzes a sample residing in a test sensor. The sample usually is in liquid form and in addition to being a biological fluid, may be the derivative of a biological fluid, such as an extract, a dilution, a filtrate, or a reconstituted precipitate. The analysis performed by the biosensor system determines the presence and/or concentration of one or more analytes, such as alcohol, glucose, uric acid, lactate, cholesterol, bilirubin, free fatty acids, triglycerides, proteins, ketones, phenylalanine or enzymes, in the biological fluid. For example, a person with diabetes may use a biosensor system to determine the A1c or glucose level in blood for adjustments to diet and/or medication.

In blood samples including hemoglobin (Hb), the presence and/or concentration of total hemoglobin (THb) and glycated hemoglobin (HbA1c) may be determined. HbA1c (%-A1c) is a reflection of the state of glucose control in diabetic patients, providing insight into the average glucose control over the three months preceding the test. For diabetic individuals, an accurate measurement of %-A1c assists in determining how well the patient is controlling blood glucose levels with diet and/or medication over a longer term than provided by an instantaneous measure of blood glucose level. As an instantaneous blood glucose measurement does not indicate blood glucose control other than when the measurement is made.

Biosensor systems may be designed to analyze one or more analytes and may use different volumes of biological fluids. Some systems may analyze a single drop of blood, such as from 0.25-15 microliters (μL) in volume. Biosensor systems may be implemented using bench-top, portable, and like measurement devices. Portable measurement devices may be hand-held and allow for the identification and/or quantification of one or more analytes in a sample. Examples of portable measurement systems include the Contour® meters of Bayer HealthCare in Tarrytown, N.Y., while examples of bench-top measurement systems include the Electrochemical Workstation available from CH Instruments in Austin, Tex.

Biosensor systems may use optical and/or electrochemical methods to analyze the biological fluid. In some optical systems, the analyte concentration is determined by measuring light that has interacted with or been absorbed by a light-identifiable species, such as the analyte or a reaction or product formed from a chemical indicator reacting with the analyte. In other optical systems, a chemical indicator fluoresces or emits light in response to the analyte when illuminated by an excitation beam. The light may be converted into an electrical output signal, such as current or potential, which may be similarly processed to the output signal from an electrochemical system. In either optical system, the system measures and correlates the light with the analyte concentration of the sample.

In light-absorption optical systems, the chemical indicator produces a reaction product that absorbs light. A chemical indicator such as tetrazolium along with an enzyme such as diaphorase may be used. Tetrazolium usually forms formazan (a chromagen) in response to the redox reaction of the analyte. An incident input beam from a light source is directed toward the sample. The light source may be a laser, a light emitting diode, or the like. The incident beam may have a wavelength selected for absorption by the reaction product. As the incident beam passes through the sample, the reaction product absorbs a portion of the incident beam, thus attenuating or reducing the intensity of the incident beam. The incident beam may be reflected back from or transmitted through the sample to a detector. The detector collects and measures the attenuated incident beam (output signal). The amount of light attenuated by the reaction product is an indication of the analyte concentration in the sample.

In light-generated optical systems, the chemical indicator fluoresces or emits light in response to the analyte redox reaction. A detector collects and measures the generated light (output signal). The amount of light produced by the chemical indicator is an indication of the analyte concentration in the sample and is represented as a current or potential from the detector.

An example of an optical system using reflectance is a laminar flow %-A1c system that determines the concentration of A1c hemoglobin in blood. These systems use immunoassay chemistry where the blood is introduced to the test sensor of the biosensor system where it reacts with reagents and then flows along a reagent membrane. When contacted by the blood, A1c antibody coated color beads release and move along with the blood to a detection Zone 1. Because of the competition between the A1c in the blood sample and an A1c peptide present in detection Zone 1 for the color beads, color beads not attached to the A1c antibody are captured at Zone 1 and are thus detected as the A1c signal from the change in reflectance. The total hemoglobin (THb) in the blood sample also is reacting with other blood treatment reagents and moves downstream into detection Zone 2, where it is measured at a different wavelength. For determining the concentration of A1c in the blood sample, the reflectance signal is proportional to the A1c analyte concentration (%-A1c), but is affected by the THb content of the blood. For the THb measurement, however, the reflectance in Zone 2 is inversely proportional to the THb (mg/mL) of the blood sample, but is not appreciably affected by the A1c content of the blood.

In electrochemical systems, the analyte concentration of the sample is determined from an electrical signal generated by an oxidation/reduction or redox reaction of the analyte or a measurable species responsive to the analyte concentration when an input signal is applied to the sample. The input signal may be a potential or current and may be constant, variable, or a combination thereof such as when an AC signal is applied with a DC signal offset. The input signal may be applied as a single pulse or in multiple pulses, sequences, or cycles. An enzyme or similar species may be added to the sample to enhance the electron transfer from the analyte during the redox reaction. The enzyme or similar species may react with a single analyte, thus providing specificity to a portion of the generated output signal. A redox mediator may be used as the measurable species to maintain the oxidation state of the enzyme and/or assist with electron transfer from the analyte to an electrode. Thus, during the redox reaction, an enzyme or similar species may transfer electrons between the analyte and the redox mediator, while the redox mediator transfers electrons between itself and an electrode of the test sensor.

Electrochemical biosensor systems usually include a measurement device having electrical contacts that connect with the electrical conductors of the test sensor. The conductors may be made from conductive materials, such as solid metals, metal pastes, conductive carbon, conductive carbon pastes, conductive polymers, and the like. The electrical conductors connect to working and counter electrodes, and may connect to reference and/or other electrodes that extend into a sample reservoir depending on the design of the test sensor. One or more electrical conductors also may extend into the sample reservoir to provide functionality not provided by the electrodes.

In many biosensor systems, the test sensor may be adapted for use outside, inside, or partially inside a living organism. When used outside a living organism, a sample of the biological fluid may be introduced into a sample reservoir in the test sensor. The test sensor may be placed in the measurement device before, after, or during the introduction of the sample for analysis. When inside or partially inside a living organism, the test sensor may be continually immersed in the sample or the sample may be intermittently introduced to the test sensor. The test sensor may include a reservoir that partially isolates a volume of the sample or be open to the sample. When open, the test sensor may take the form of a fiber or other structure placed in contact with the biological fluid. Similarly, the sample may continuously flow through the test sensor, such as for continuous monitoring, or be interrupted, such as for intermittent monitoring, for analysis.

The measurement device of an electrochemical biosensor system applies an input signal through the electrical contacts to the electrical conductors of the test sensor. The electrical conductors convey the input signal through the electrodes into the sample present in the sample reservoir. The redox reaction of the analyte generates an electrical output signal in response to the input signal. The electrical output signal from the test sensor may be a current (as generated by amperometry or voltammetry), a potential (as generated by potentiometry/galvanometry), or an accumulated charge (as generated by coulometry). The measurement device may have the processing capability to measure and correlate the output signal with the presence and/or concentration of one or more analytes in the sample.

In coulometry, a potential is applied to the sample to exhaustively oxidize or reduce the analyte. A biosensor system using coulometry is described in U.S. Pat. No. 6,120,676. In amperometry, an electric signal of constant potential (voltage) is applied to the electrical conductors of the test sensor while the measured output signal is a current. Biosensor systems using amperometry are described in U.S. Pat. Nos. 5,620,579; 5,653,863; 6,153,069; and 6,413,411. In voltammetry, an electric signal of varying potential is applied to a sample of biological fluid, while the measured output is current. In gated amperometry and gated voltammetry, pulsed inputs are used as described in WO 2007/013915 and WO 2007/040913, respectively.

Primary output signals are responsive to the analyte concentration of the sample and are obtained from an analytic input signal. Output signals that are substantially independent of signals responsive to the analyte concentration of the sample include signals responsive to temperature and signals substantially responsive to interferents, such as the hematocrit or acetaminophen content of a blood sample when the analyte is glucose, for example. Output signals substantially not responsive to analyte concentration may be referred to as secondary output signals, as they are not primary output signals responsive to the alteration of light by the analyte or analyte responsive indicator, the electrochemical redox reaction of the analyte, or the electrochemical redox reaction of the analyte responsive redox mediator. Secondary output signals are responsive to the physical or environmental characteristics of the biological sample. Secondary output signals may arise from the sample or from other sources, such as a thermocouple that provides an estimate of an environmental characteristic of the sample. Thus, secondary output signals may be determined from the analytic input signal or from another input signal.

When arising from the sample, secondary output signals may be determined from the electrodes used to determine the analyte concentration of the sample, or from additional electrodes. Additional electrodes may include the same reagent composition as the electrodes used to determine the analyte concentration of the sample, a different reagent composition, or no reagent composition. For example, a reagent composition may be used that reacts with an interferent or an electrode lacking reagent composition may be used to study one or more physical characteristics of the sample, such as whole blood hematocrit.

During sample analysis, there may be more than one stimulus affecting the primary output signal analyzed by the measurement device. These stimuli include the analyte concentration of the sample, the physical characteristics of the sample, the environmental aspects of the sample, the manufacturing variations between test sensor lots, and the like. Since the primary goal of the analysis is to determine the presence and/or concentration of the analyte in the sample, the analyte concentration of the sample is referred to as the primary stimulus. All other stimuli that affect the output signal are referred to as extraneous stimulus. Thus, the primary output signals include a major effect from the primary stimulus—the analyte concentration of the sample—but also include some effect from one or more extraneous stimulus. In contrast, the secondary output signals include a major effect from one or more extraneous stimulus, and may or may not include a major effect from the primary stimulus.

The measurement performance of a biosensor system is defined in terms of accuracy and precision. Accuracy reflects the combined effects of systematic and random error components. Systematic error, or trueness, is the difference between the average value determined from the biosensor system and one or more accepted reference values for the analyte concentration of the biological fluid. Trueness may be expressed in terms of mean bias, with larger mean bias values representing lower trueness and thereby contributing to less accuracy. Precision is the closeness of agreement among multiple analyte readings in relation to a mean. One or more error in the analysis contributes to the bias and/or imprecision of the analyte concentration determined by the biosensor system. A reduction in the analysis error of a biosensor system therefore leads to an increase in accuracy and/or precision and thus an improvement in measurement performance.

Bias may be expressed in terms of "absolute bias" or "percent bias". Absolute bias is the difference between the determined concentration and the reference concentration, and may be expressed in the units of the measurement, such as mg/dL, while percent bias may be expressed as a percentage of the absolute bias value over the reference concentration, or expressed as a percentage of the absolute bias over either the cut-off concentration value or the reference concentration of the sample. For example, if the cut-off concentration value is 100 mg/dL, then for glucose concentrations less than 100 mg/dL, percent bias is defined as (the absolute bias over 100 mg/dL)*100; for glucose concentrations of 100 mg/dL and higher, percent bias is defined as the absolute bias over the accepted reference value of analyte concentration*100.

Accepted reference values for the analyte glucose in blood samples are preferably obtained with a reference instrument, such as the YSI 2300 STAT PLUS™ available from YSI Inc., Yellow Springs, Ohio. Other reference instruments and ways to determine percent bias may be used for other analytes. For the %-A1c measurements, the error may be expressed as either absolute bias or percent bias against the %-A1c reference value for the therapeutic range of 4-12%. Accepted reference values for the %-A1c in blood samples may be obtained with a reference instrument, such as the Tosoh G7 instrument available from Tosoh Corp, Japan.

Hematocrit bias refers to the average difference (systematic error) between the reference glucose concentration obtained with a reference instrument and experimental glucose readings obtained from the measurement device and the test sensor of a biosensor system for samples containing differing hematocrit levels. The difference between the reference and values obtained from the biosensor system results from the varying hematocrit level between specific blood samples and may be generally expressed as a percentage as follows: % Hct-Bias=$100\% \times (G_m - G_{ref})/G_{ref}$, where $G_m$ is the determined glucose concentration at a specific hematocrit level and $G_{ref}$ is the reference glucose concentration at a sample hematocrit level. The larger the absolute value of the % Hct-bias, the more the hematocrit level of the sample (expressed as % Hct, the percentage of red blood cell volume/sample volume) is reducing the accuracy of the glucose concentration determined from the biosensor system.

For example, if different blood samples containing identical glucose concentrations, but having hematocrit levels of 20, 40, and 60%, are analyzed, three different glucose concentrations will be reported by a biosensor system based on one set of calibration constants (slope and intercept of the 40% hematocrit containing blood sample, for instance). Thus, even though the glucose concentration of the different blood samples is the same, the system will report that the 20% hematocrit sample contains more glucose than the 40% hematocrit sample, and that the 60% hematocrit sample contains less glucose than the 40% hematocrit sample. "Hematocrit sensitivity" is an expression of the degree to which changes in the hematocrit level of a sample affect the bias values for an analysis performed with the biosensor system. Hematocrit sensitivity may be defined as the numerical values of the percent biases per percent hematocrit, thus bias/%-bias per % Hct.

Biosensor systems may provide an output signal during the analysis of the biological fluid including error from multiple error sources. These error sources contribute to the total error, which may be reflected in an abnormal output signal, such as when one or more portions or the entire output signal is non-responsive or improperly responsive to the analyte concentration of the sample.

The total error in the output signal may originate from one or more error contributors, such as the physical characteristics of the sample, the environmental aspects of the sample, the operating conditions of the system, the manufacturing variation between test sensor lots, and the like. Physical characteristics of the sample include hematocrit (red blood cell) concentration, interfering substances, such as lipids and proteins, and the like. Interfering substances for glucose analyses also may include ascorbic acid, uric acid, acetaminophen, and the like. Environmental aspects of the sample include temperature, oxygen content of the air, and the like. Operating conditions of the system include underfill conditions when the sample size is not large enough, slow-filling of the test sensor by the sample, intermittent electrical contact between the sample and one or more electrodes of the test sensor, degradation of the reagents that interact with the analyte after the test sensor was manufactured, and the like. Manufacturing variations between test sensor lots include changes in the amount and/or activity of the reagents, changes in the electrode area and/or spacing, changes in the electrical conductivity of the conductors and electrodes, and the like. A test sensor lot is preferably made in a single manufacturing run where lot-to-lot manufacturing variation is substantially reduced or eliminated. There may be other contributors or a combination of error contributors that cause error in the analysis.

Percent bias, mean percent bias, percent bias standard deviation (SD), percent coefficient of variance (%-CV), and hematocrit sensitivity are independent ways to express the measurement performance of a biosensor system. Additional ways may be used to express the measurement performance of a biosensor system.

Percent bias is a representation of the accuracy of the biosensor system in relation to a reference analyte concentration, while the percent bias standard deviation reflects the accuracy of multiple analyses, with regard to error arising from the physical characteristics of the sample, the environmental aspects of the sample, the operating conditions of the system, and the manufacturing variations between test sensors. Thus, a decrease in percent bias standard deviation represents an increase in the measurement performance of the biosensor system across multiple analyses. The percent coefficient of variance may be expressed as 100%*(SD of a set of samples)/(the average of multiple readings taken from the same set of samples) and reflects precision of multiple analyses. Thus, a decrease in percent bias standard deviation represents an increase in the measurement performance of the biosensor system across multiple analyses.

Increasing the measurement performance of the biosensor system by reducing error from these or other sources means that more of the analyte concentrations determined by the biosensor system may be used for accurate therapy by the patient when blood glucose is being monitored, for example. Additionally, the need to discard test sensors and repeat the analysis by the patient also may be reduced.

Biosensor systems may have a single source of uncompensated output signals responsive to a redox or light-based reaction of the analyte, such as the counter and working electrodes of an electrochemical system. Biosensor systems also may have the optional ability to determine or estimate temperature, such as with one or more thermocouples or other means. In addition to these systems, biosensor systems also may have the ability to generate secondary output signals external to those from the analyte or from a mediator responsive to the analyte. For example, in an electrochemical test sensor, one or more electrical conductors also may extend into the sample reservoir to provide functionality not provided by the working and counter electrodes. Such conductors may lack one or more of the working electrode reagents, such as the mediator, thus allowing for the subtraction of a background interferent signal from the working electrode signal.

Many biosensor systems include one or more methods to compensate for errors associated with an analysis, thus attempting to improve the measurement performance of the biosensor system. Compensation methods may increase the measurement performance of a biosensor system by providing the biosensor system with the ability to compensate for error in the analyses, thus increasing the accuracy and/or precision of the concentration values obtained from the system. Conventional error compensation methods for physical and environmental error contributors are traditionally developed in a laboratory as these types of errors can be reproduced in a controlled environment.

How the measurement device of the biosensor system is calibrated in the laboratory affects the measurement performance of the system in the hands of the user. Thus, an ongoing concern in the context of calibrating a measurement device is that of all the error parameters that may affect the measurement performance of the measurement device in use, which error parameters should be calibrated for in the laboratory before the measurement device is used for analyzing the analyte concentration of samples.

Error parameters are variables, the values of which are determined from the analysis, such as the intermediate signals from the primary output signal, or from secondary output signals independent of the analyte responsive output signal, such as thermocouples, additional electrodes, and the like. Error parameters may be any variables responsive to one or more errors in the output signal. Thus, these variables with their discrete values may be the currents or potentials measured from the intermediate signals from a primary output signal, or from secondary output signals, such as from thermocouple currents or voltages, additional electrode currents or voltages, and the like. Other error parameters may be determined from these or other primary or secondary output signals.

A point of diminishing returns or even poorer measurement performance may result if the measurement device is calibrated for too many or non-optimal error parameters. Furthermore, the more parameters that are considered in the calibration, the less useful the calibration information stored in the measurement device may be for later compensation of the analysis from error parameters determined during the analysis. These calibration issues become even more complex when the analysis being performed includes multiple output signals including analyte concentration-responsive (primary output signals) and/or non-analyte responsive signals (secondary output signals). The present invention avoids or ameliorates at least some of the disadvantages of measurement devices using conventional calibration techniques.

SUMMARY

In one aspect, the invention provides a method for determining an analyte concentration in a sample that includes generating at least one output signal from a sample; measuring at least one analyte responsive output signal value from the at least one output signal, where the at least one analyte responsive output signal value is affected by at least one extraneous stimulus; measuring at least one extraneous stimulus responsive output signal from the sample; determining at least one quantified extraneous stimulus value in response to the at least one extraneous stimulus output signal; determining at least one normalizing value from at least one normalizing relationship; determining at least one normalized analyte responsive output signal value in response to the at least one analyte responsive output signal value and the at least one normalizing value; and determining at least one analyte concentration in the sample in response to at least one normalized reference correlation and the at least one normalized analyte responsive output signal.

In another aspect of the invention, there is a method for calibrating a measurement device of a biosensor system that includes measuring at least two analyte responsive output signals from a sample, where the analyte responsive output signals are affected by at least one extraneous stimulus; determining a reference correlation between at least one reference sample analyte concentration and the at least two analyte responsive output signals; measuring at least one extraneous stimulus responsive output signal from the sample; determining at least two quantified extraneous stimulus values from the at least one extraneous stimulus responsive output signal; determining a normalizing relationship between the at least two analyte responsive output signals and the at least two quantified extraneous stimulus values; determining a normalizing value from the normalizing relationship and the at least two quantified extraneous stimulus values; determining at least two normalized analyte responsive output signals from the at least two analyte responsive output signals and the normalizing value; and determining a normalized reference correlation between the at least two normalized analyte responsive output signals and the least one reference sample analyte concentration.

In another aspect of the invention, there is an analyte measurement device that includes electrical circuitry connected to a sensor interface, where the electrical circuitry includes a processor connected to a signal generator and a storage medium; where the processor is capable of measuring at least one analyte responsive output signal value from a sample, where the at least one analyte responsive output signal value is affected by at least one extraneous stimulus; where the processor is capable of measuring at least one extraneous stimulus responsive output signal from the sample; where the processor is capable of determining at least one quantified extraneous stimulus value in response to the at least one extraneous stimulus output signal; where the processor is capable of determining at least one normalizing value from at least one normalizing relationship; where the processor is capable of determining at least one normalized analyte responsive output signal value in response to the at least one analyte responsive output signal value and the at least one normalizing value; and where the processor is capable of determining at least one analyte concentration in the sample in response to at least one normalized reference correlation and the at least one normalized analyte responsive output signal.

In another aspect of the invention, there is a biosensor system for determining an analyte concentration in a sample that includes a test sensor having a sample interface adjacent to a reservoir formed by a base, where the test sensor is capable of generating at least one output signal from a sample; and a measurement device having a processor connected to a sensor interface, the sensor interface having electrical communication with the sample interface, and the processor having electrical communication with a storage medium; where the processor is capable of measuring at least one analyte responsive output signal value from the at least one output signal, where the at least one analyte responsive output signal value is affected by at least one extraneous stimulus; where the processor is capable of measuring at least one extraneous stimulus responsive output signal from the sample; where the processor is capable of determining at least one quantified extraneous stimulus value in response to the at least one extraneous stimulus output signal; where the processor is capable of determining at least one normalizing value from at least one normalizing relationship; where the processor is capable of determining at least one normalized analyte responsive output signal value in response to the at least one analyte responsive output signal value and the at least one normalizing value; and where the processor is capable of determining at least one analyte concentration in the sample in response to at least one normalized reference correlation and the at least one normalized analyte responsive output signal.

BRIEF DESCRIPTION OF THE DRAWINGS

The invention can be better understood with reference to the following drawings and description. The components in the figures are not necessarily to scale, emphasis instead being placed upon illustrating the principles of the invention.

FIG. 1A represents a calibration method of determining calibration information for incorporation into a measurement device with a reduced extraneous stimulus effect.

FIG. 1C represents an analysis method of determining the analyte concentration of a sample with a reduced extraneous stimulus effect using a normalized reference correlation.

DETAILED DESCRIPTION

Figure 1B:
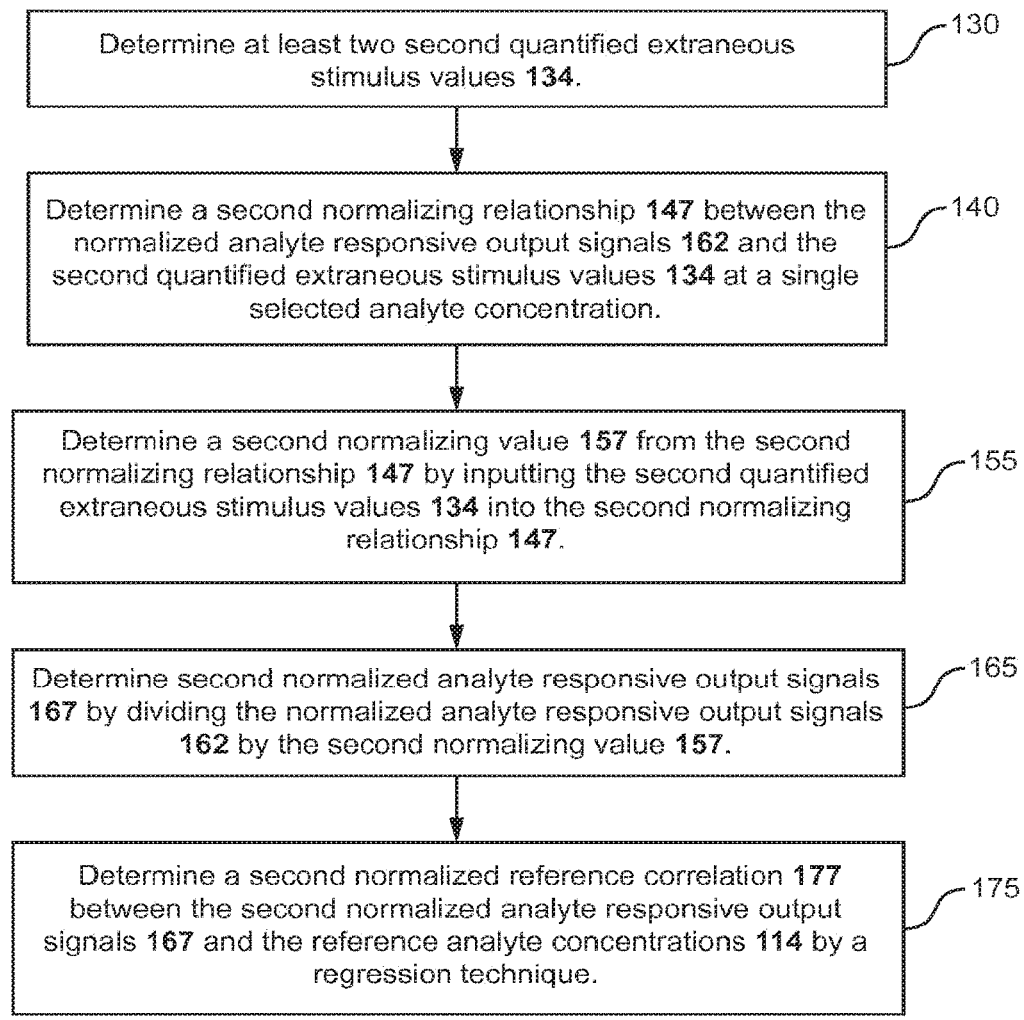
FIG. 1B represents an optional calibration method of also considering a second extraneous stimulus with the calibration information.

Measurement devices in biosensor systems that are used to determine the presence and/or concentration of an analyte in a sample include normalized calibration information relating output signal or signals the device generates in response to the analyte concentration of the sample to previously determined reference sample analyte concentrations. The measurement devices use this normalized calibration information to relate one or more output signals from an electrochemical or optical analysis of a sample to the presence and/or concentration of one or more analytes in the sample.

The present application discloses methods to determine normalized calibration information in a factory, laboratory or similar setting for use in sample analysis of analyte concentration(s), methods to determine the analyte concentration(s) of a sample using normalized calibration information that is stored in a measurement device of a biosensor system for use during sample analysis, and a biosensor system that uses normalized calibration information to determine the presence and/or concentration of the analyte(s) in the sample. The normalized calibration information includes a normalizing relationship used to determine normalized output signals from measured output signals and a normalized reference correlation relating the normalized output signals determined during the analysis to a reference sample analyte concentration. The normalized calibration information is useful in biosensor systems that generate at least one primary output signal responsive to an analyte but include or are affected by error from at least one extraneous stimulus and that generate at least one secondary output signal responsive to the at least one extraneous stimulus During sample analysis, the primary stimulus and one or more extraneous stimulus affect the one or more output signals analyzed by the measurement device. The primary stimulus is the analyte concentration of the sample. The extraneous stimulus includes all other stimuli (except the analyte concentration) that affect the output signal such as the physical characteristics of the sample, the environmental aspects of the sample, manufacturing variations between test sensor lots, and the like. The one or more output signals analyzed by the measurement device may include primary output signals and secondary output signals. The primary output signals include a major effect from the primary stimulus—the analyte concentration of the sample—but also include some effect from one or more extraneous stimulus. In contrast, the secondary output signals include a major effect from the extraneous stimuli, and may or may not include a major effect from the primary stimulus. Preferably, the secondary output signals are solely responsive to the one or more extraneous stimulus.

The measurement of %-A1c in blood samples, thus the concentration of glycated hemoglobin (%-A1c or A1c) in the total hemoglobin (THb) content of a blood sample, may be accomplished by an immunoassay method using a laminar flow analysis. Conventionally, in the laminar flow analysis two independent signals are measured, primary output signals for the A1c and secondary output signals for the THb. In this type of A1c system, the Zone 1 detectors provide the primary output signal while the Zone 2 detectors provide the secondary output signal. The primary output signals from the Zone 1 detector/s depends on the A1c concentration of the sample, but also on the THb concentration of the sample. The secondary output signals from the Zone 2 detector/s depend on the THb concentration of the sample, but are substantially independent of the A1c concentration of the sample.

Conventional calibration in these systems focuses on establishing a relationship between the known %-A1c value of reference samples, the reflectance primary output signals determined from the Zone 1 detector/s of the measurement device responsive to A1c when these samples are analyzed by the biosensor system, and the secondary output reflectance signals determined from the Zone 2 detector/s of the measurement device responsive to the THb content of the sample when these samples are analyzed by the biosensor system. Thus, there are three stimuli for potential consideration in determining the calibration information to store in the measurement device for later use during an analysis (reference sample analyte concentration, primary output signals from the measurement device, and secondary output signals from the measurement device).

In contrast to such conventional methods, a significant benefit of the presently disclosed calibration methods in an A1c biosensor system arises from the ability to use the laboratory determined calibration information in later compensation techniques when two of the stimuli (reference sample analyte concentration (%-A1c, primary stimulus) and secondary THb output signals (an extraneous stimulus)) are reduced to one (reference sample analyte concentration for %-A1c). One method of accomplishing this reduction of stimuli is through the described normalization methods.

The normalization method reduces the dependence of the primary output A1c signal from the measurement device on THb sample concentration by generating a normalized output signal from the A1c responsive reflectance values determined by the measurement device. Then a normalized reference correlation is determined between the generated normalized output signals and the reference sample analyte concentrations. The normalization relationship used to determine the normalized output signals and the normalized reference correlation are stored in the measurement device. In use, the primary output signals measured from the Zone 1 detector/s of the measurement device as normalized by the described normalization procedure remain responsive to A1c, but become substantially independent of the secondary output signals measured from the Zone 2 detector/s responsive to the total hemoglobin content of the sample (THb).

In a glucose analysis system, calibration generally focuses on establishing a relationship between the known reference sample analyte concentrations for glucose, the electrical or optical primary output signals determined from the sample, and the secondary output signals responsive to temperature and/or the hematocrit (Hct) content of the sample. These secondary output signals may be determined from a thermistor, a dedicated Hct electrode, and the like, or from one or more estimates of these values originating from the primary output signals.

In these glucose analysis systems, the electrical or optical primary output signals responsive to the glucose concentration of the sample also depends on the temperature of the sample and/or the Hct content of the sample. The temperature and Hct information provided by the secondary output signals of the measurement device is substantially independent of the glucose concentration of the sample. Thus, in addition to the reference sample analyte concentration, there are at least two (glucose and temperature responsive signals) or three (glucose, temperature, and Hct responsive signals) stimuli to consider for determining the calibration information to store in the measurement device for later use during an analysis.

An example of a conventional method of addressing this calibration in a glucose system is to generate a line or curve representing the reference correlation between multiple reference sample analyte concentrations for glucose and the corresponding output signals of the measurement device at a known temperature, and/or hematocrit concentration. This reference correlation is stored in the measurement device for later use during the analysis. As optical detectors convert light to a voltage and/or amperage, this process is similar for optical or electrochemical biosensor systems. Thus, a reference correlation may be determined for the known reference sample analyte concentration at 20° C. and a 40% sample Hct, for example, and stored in the measurement device. This process may be repeated for multiple Hct sample concentrations at the selected temperature, for example, and these reference correlations also stored in the measurement device. However, in this conventional technique, during the analysis the measurement device must select which of the multiple reference correlations to use or to interpolate between for a specific analysis. Thus, the measurement device is attempting to select the best reference correlation of those it has to fit the actual analysis—a process fraught with potential issues. The goal of the later analysis of a sample by the biosensor system is to transform the output signal determined by the measurement device into the analyte concentration of the sample using the previously determined reference correlation or correlations stored in the device.

In contrast to a conventional direct conversion of the output signal to a concentration by the reference correlation, a significant benefit of the presently disclosed calibration methods arises from the ability to use the laboratory determined calibration information stored in the measurement device in later compensation techniques if at least two of these stimuli (reference sample analyte concentration for glucose and secondary temperature output signals) are reduced to one (reference sample analyte concentration for glucose). For example, the temperature dependence of the reference correlation on temperature may be reduced or preferably removed through the described normalization methods to make the reference correlation unitless. Similarly, the Hct dependence of the reference correlation also may be reduced or preferably removed through the described normalization methods.

The normalization method reduces the dependence of the primary output glucose signal from the measurement device on temperature or temperature and sample %-Hct by generating a normalized output signal from the glucose responsive current values determined by the measurement device. Then a normalized reference correlation is determined between the generated normalized output signals and the reference sample analyte concentrations. The normalization relationship used to determine the normalized output signals and the normalized reference correlation are stored in the measurement device. In use, the primary output signals responsive to glucose as measured by the measurement device as normalized by the described normalization procedure remain responsive to glucose, but become substantially independent of the secondary output signals responsive to temperature or temperature and sample %-Hct.

For either analysis type, the normalization method may be represented by the following expression: Normalized Output Signal=(analyte responsive signal including the effect of one primary stimulus and at least one extraneous stimulus)/(at least one extraneous stimulus signal) where the effect of the primary stimulus is the effect the measurement device is attempting to detect and/or quantify. Thus, while two or more factors affect the outcome of the analysis, one or more factor is normalized to reduce the factors affecting the outcome of the analysis to one. The analyte responsive primary output signal may be the reflectance output from the Zone 1 detector/s of an A1c analysis system or the current output responsive to the electrochemical redox reaction of glucose or a glucose concentration responsive mediator in an electrochemical analysis system, for example. Primary output signals from other types of analyses also may be used with the normalization method. The extraneous stimulus may be THb in an A1c analysis system, for example, or temperature and/or hematocrit in a glucose analysis system, for example. Thus, the extraneous stimulus arises from the secondary output signals of the analysis.

FIG. 1A represents a calibration method 100 of determining normalized calibration information for incorporation into a measurement device of a biosensor system with a reduced stimulus effect. Preferably, the calibration method 100 is performed during factory calibration of the measurement device. The calibration method 100 also may be performed in a laboratory or similar setting. The calibration method may be performed by the measurement device, one or more analytical devices such as a computer, or a combination of the measurement and analytical devices.

Figure 2A:
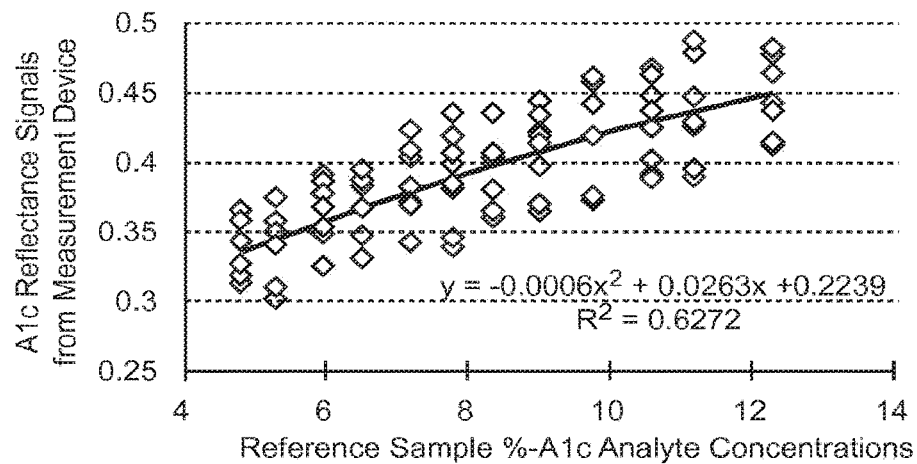
FIG. 2A shows the A1c reflectance signals recorded from the Zone 1 detector/s of the measurement device versus reference sample analyte concentrations (%-A1c) at four THb (total hemoglobin) concentrations (85 mg/mL, 125 mg/mL, 175 mg/mL, and 230 mg/mL).
Figure 4A:
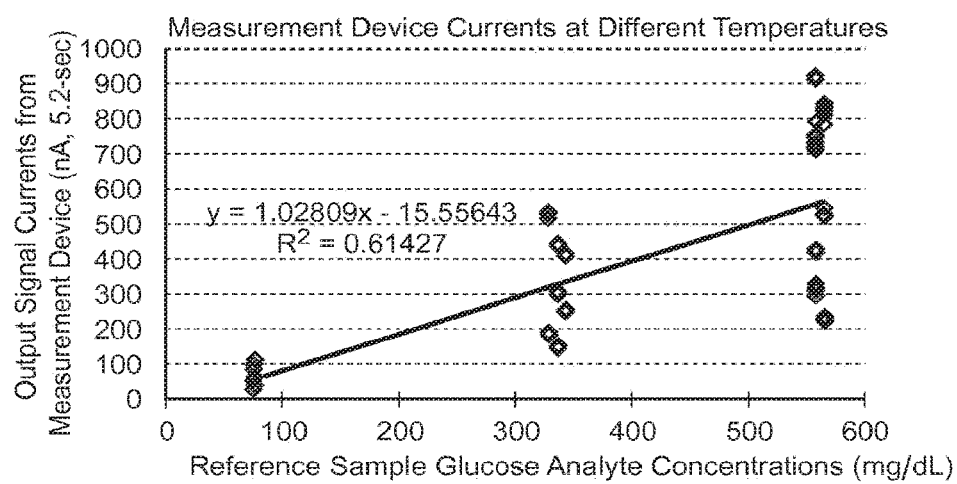
FIG. 4A plots the currents obtained from the measurement device versus reference sample analyte concentrations for glucose at different temperatures and 40% Hct.

In analyte responsive output signal measurement 110, analyte responsive output signals are measured from a reference sample, where the analyte responsive output signals are affected by at least one extraneous stimulus resulting from a physical characteristic, an environmental aspect, and/or a manufacturing variation error being incorporated into the analyte responsive output signals. At least two analyte responsive output signals are measured. Preferably, at least four, and more preferably at least 6 analyte responsive output signals are measured from the reference sample. Optical and/or electrochemical methods may be used to analyze the reference samples. FIG. 2A, as addressed further below, provides an example of the analyte responsive output signal measurement 110 in an A1c analysis system. FIG. 4A, as addressed further below, provides an example of the analyte responsive output signal measurement 110 in a glucose analysis system.

In reference correlation determination 120, a reference correlation 122 is determined between one or more reference sample analyte concentrations 124 and one or more output signals. The reference correlation 122 relates the reference sample analyte concentrations 124 to the output signals as determined by the measurement device 126. The reference sample analyte concentration of the reference samples may be determined using a reference instrument, by mixing or altering known sample analyte concentrations, and the like.

Figure 2B:
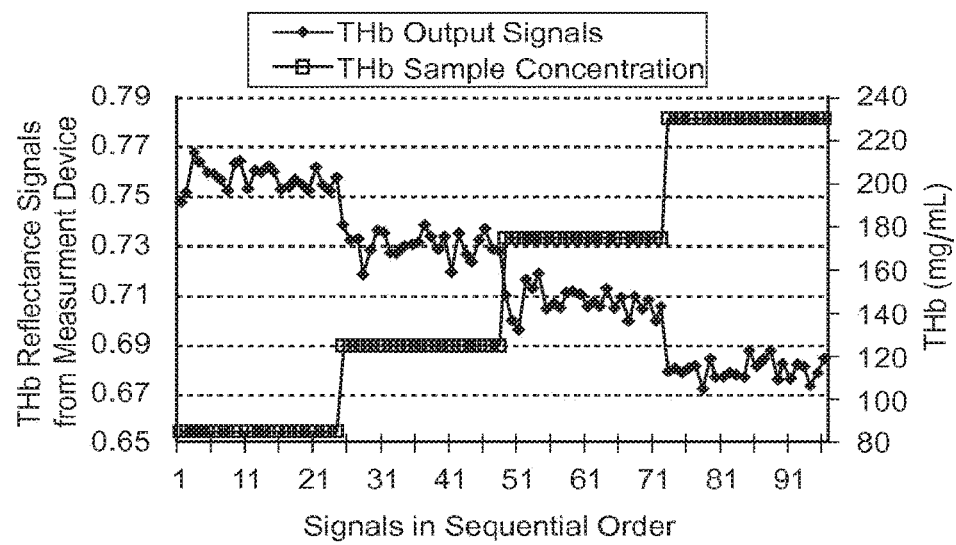
FIG. 2B shows the comparatively constant THb output signals at four levels of THb reference sample concentrations (85 mg/mL, 125 mg/mL, 175 mg/mL, and 230 mg/mL) as determined from the Zone 2 detectors of the measurement device.

In extraneous stimulus quantification 130, one or more extraneous stimulus responsive output signals are measured from the reference samples and the extraneous stimulus quantified to determine at least two quantified extraneous stimulus values 132. The stimulus responsive output signals may be measured concurrently with the analyte responsive output signals or at different times. Preferably, the stimulus responsive output signals are measured concurrently with the analyte responsive output signals. FIG. 2B, as addressed further below, provides an example of the extraneous stimulus quantification 130 in an A1c analysis system. In a glucose system, for example as represented in Table 3, when temperature is the extraneous stimulus, multiple analyses are performed at a target temperature and the actual temperature for each analysis averaged.

The extraneous stimulus signals may be directly quantified, such as when an optical detector or electrode outputs a specific voltage and/or amperage. The extraneous stimulus signals may be indirectly quantified, such as when a thermistor provides a specific voltage and/or amperage that is reported as a temperature in degrees Celsius, for example. The extraneous stimulus signals also may be indirectly quantified, such as when the Hct concentration of a sample is determined from a specific voltage and/or amperage measured from an Hct electrode, for example. The extraneous stimulus signals may be directly or indirectly quantified and then modified to provide the quantified extraneous stimulus values 132, such as when the directly or indirectly quantified extraneous stimulus value is transformed into a concentration. The quantified extraneous stimulus values 132 may be determined by averaging multiple values, such as multiple temperature readings recorded at the same target temperature. The extraneous stimulus may be quantified through other techniques. For example, analysis method 200, as described further below provides an example of extraneous stimulus quantification.

Figure 2C:
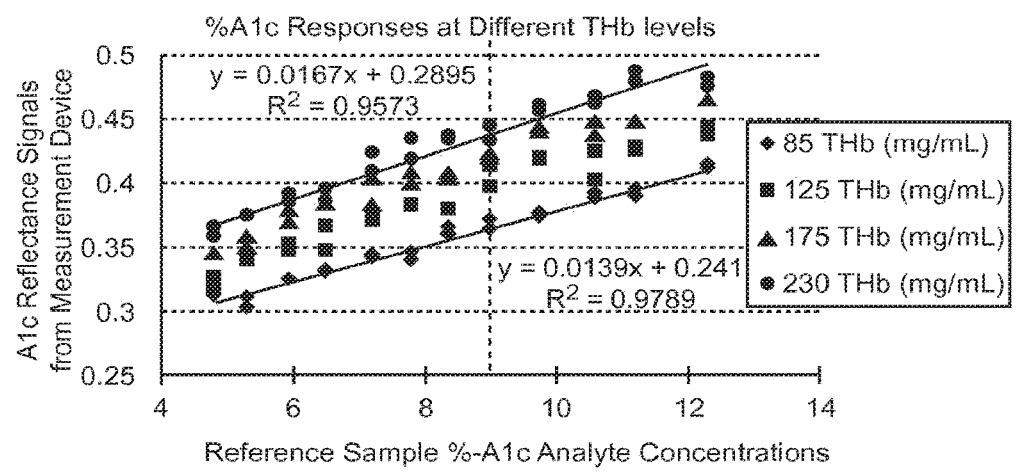
FIG. 2C shows the individual A1c reflectance signals recorded from the Zone 1 detector/s of the measurement device separated for the four different THb concentrations in blood samples.
Figure 4B:
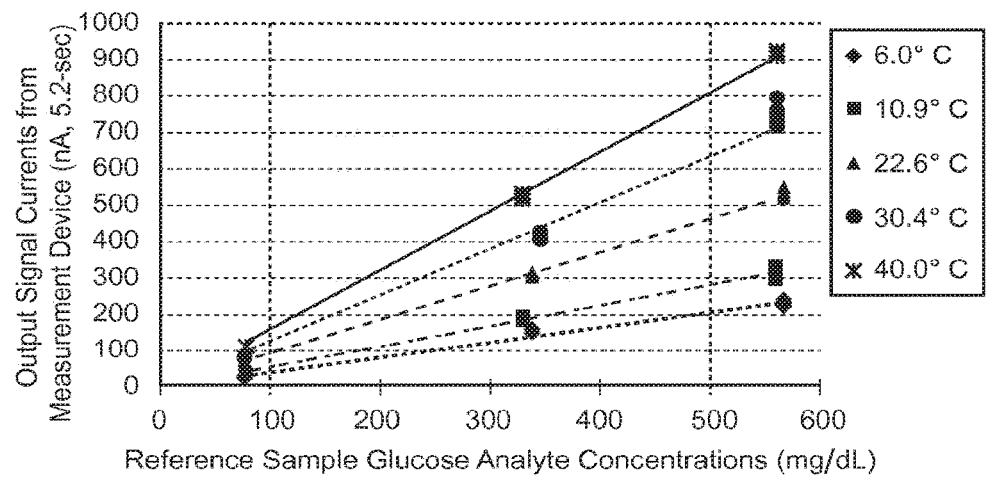
FIG. 4B separates these primary output signal currents by the temperature at which they were recorded.

In normalizing relationship determination 140, a normalizing relationship 142 is determined between the analyte responsive output signals and the quantified extraneous stimulus values 132 for the analyte concentration of the one or more reference sample analyte concentrations selected. Preferably, a regression technique is applied to the analyte responsive output signals and the quantified extraneous stimulus values 132 to determine the normalizing relationship at single selected analyte concentration. FIG. 2C, as addressed further below, provides an example of how a single analyte concentration was selected in an A1c analysis system and used to determine synthesized extraneous stimulus responsive output signals responsive to the quantified extraneous stimulus signals for THb. FIG. 4B, as addressed further below, provides an example of how one of two analyte concentrations was selected in a glucose analysis system and used to determine synthesized extraneous stimulus responsive output signals responsive to the quantified extraneous stimulus signals for temperature. Thus, a synthesized extraneous stimulus responsive output signal was determined from the primary output signals at a single selected sample analyte concentration. The synthesized extraneous stimulus responsive output signal may be thought of as the extraneous stimulus responsive output signal extracted from the combined primary output signal from the measurement device that includes both the primary and the extraneous stimulus. Similarly, the normalizing relationship 142 may be thought of as a reference correlation for the extraneous stimulus.

Figure 2D:
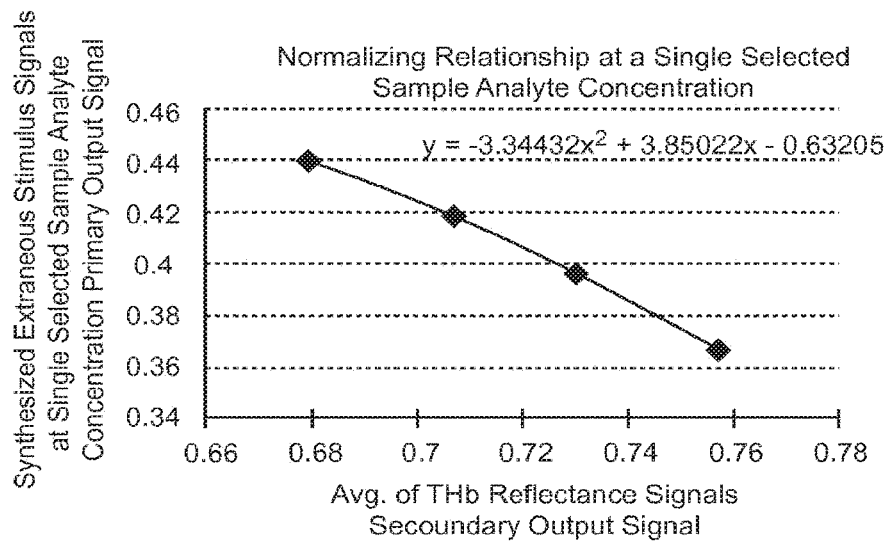
FIG. 2D also provides an example of determining the normalization relationship 140, which establishes the correlation between the synthesized extraneous stimulus responsive output signals at a single A1c concentration and the secondary output signals responsive to the sample THb concentrations.
Figure 4C:
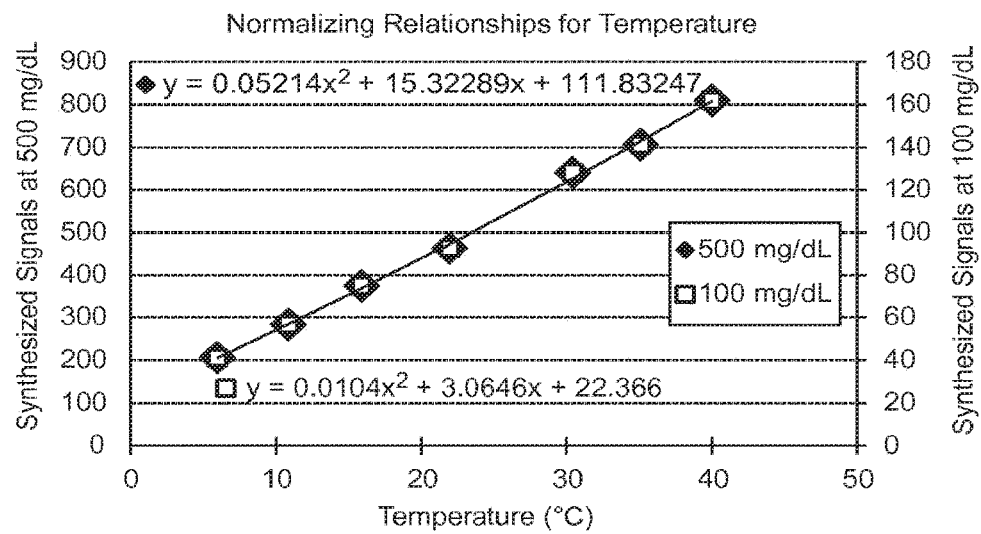
FIG. 4C shows the correlations between the synthesized extraneous stimulus responsive output signals obtained at two separate single glucose concentration of 100 and 500 mg/dL versus the quantified extraneous stimulus (temperatures) to determine the normalization relationships.

FIG. 2D, as addressed further below, provides an example of how the normalizing relationship determination 140 may be implemented in an A1c analysis system using the synthesized extraneous stimulus responsive output signal values. An example normalizing relationship as determined for the A1c analysis system is shown in FIG. 2D. FIG. 4C, as addressed further below, provides an example of how the normalizing relationship determination 140 may be implemented in a glucose analysis system using the synthesized extraneous stimulus responsive primary output signals. Example normalizing relationships as determined for the glucose analysis system also are shown in FIG. 4G.

Linear or non-linear (such as polynomial) regression techniques may be used to determine the normalizing relationship 142. Linear or non-linear regression techniques include those available in the MINITAB® version 14 or version 16 statistical packages (MINTAB, INC., State College, Pa.), Microsoft Excel, or other statistical analysis packages providing regression techniques. Preferably, polynomial regression is used to determine the normalizing relationship 142. For example in MS Excel version 2010, the Linear Trendline Option accessible through the Trendline Layout Chart Tool may be selected to perform linear regression, while the Polynomial Trendline Option may be chosen to perform a non-linear polynomial regression. Other regression techniques may be used to determine the normalizing relationship 142. The normalizing relationship 142 is preferably stored in the measurement device as a portion of the calibration information.

When linear regression is used, the normalizing relationship 142 will be in the form of $Y=mX+b$, where m is the slope and b is the intercept of the regression line. When non-linear regression is used, the normalizing relationship 142 will be in a form of $Y=b_2*X^2+b_1*X+b_0$, and the like, where $b_2$, $b_1$ and $b_0$ are the coefficients of the polynomial. In both the linear or polynomial regression equations, Y is the calculated synthesized extraneous stimulus responsive output signal responsive to the extraneous stimulus portion of the primary output signal at a single selected analyte concentration, and X is the quantified extraneous stimulus signals/values. When a value of X (the quantified extraneous stimulus signal value) is entered into either one of the relationships (linear or polynomial equations), an output value Y, representing the normalizing value (NV) is generated from the normalizing relationship.

If a second extraneous stimulus is adversely affecting the analyte responsive output signals and will be addressed by the calibration information, the normalizing relationship determination 140 is repeated for a second extraneous stimulus. An example of how a second normalizing relationship may be determined to address a second extraneous stimulus is found regarding FIG. 5, as addresses further below.

In normalizing value determination 150, a normalizing value 152 is determined from the normalizing relationship 142 by inputting the quantified extraneous stimulus values 132 into the normalizing relationship 142 and solving for the normalizing value 152.

Figure 2E:
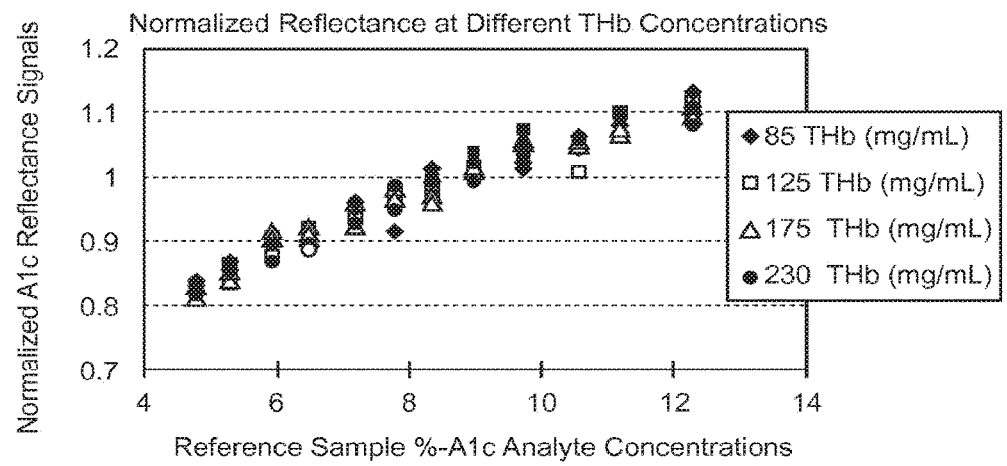
FIG. 2E provides an example of the determination of normalized analyte responsive output signals from the normalizing value.
Figure 4D:
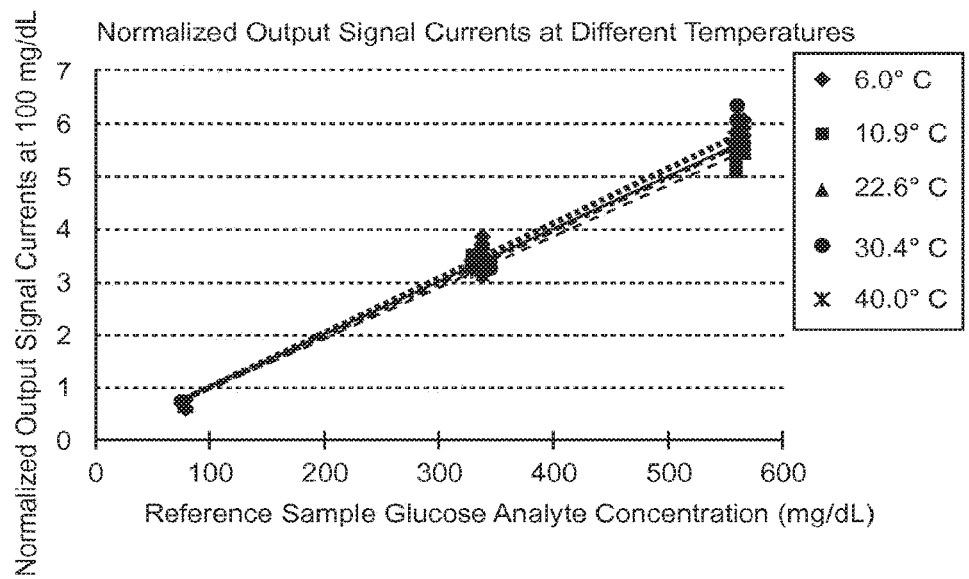
FIG. 4D provides an example of the determination of normalized analyte responsive output signals from the normalizing value at 100 mg/dL.

In normalized output signal determination 160, one or more normalized analyte responsive output signals are determined from one or more analyte responsive output signals and the normalizing value. Preferably, the analyte responsive output signals are divided by the normalizing value 152 to provide normalized analyte responsive output signals 162. This preferably reduces the effect of the extraneous stimulus on the analyte responsive output signals. FIG. 2E, as addressed further below, provides an example of the normalized output signal determination 160 in an A1c analysis system. FIG. 4D, as addressed further below, provides an example of the normalized output signal determination 160 in a glucose analysis system at a single selected sample analyte concentration (100 mg/dL).

In normalized reference correlation determination 170, a normalized reference correlation 172 is determined between the normalized analyte responsive output signals 162 and the reference sample analyte concentrations 124. Preferably, a regression technique is applied to the normalized analyte responsive output signals 162 and the reference sample analyte concentrations 124 to determine the normalized reference correlation 172. Linear or non-linear (such as polynomial) regression techniques may be used, such as those available in the MINITAB® version 14 or version 16 statistical packages (MINTAB, INC., State College, Pa.), Microsoft Excel, or another statistical analysis package providing regression techniques. Preferably, polynomial regression is used to determine the normalized reference correlation 172.

Figure 2F:
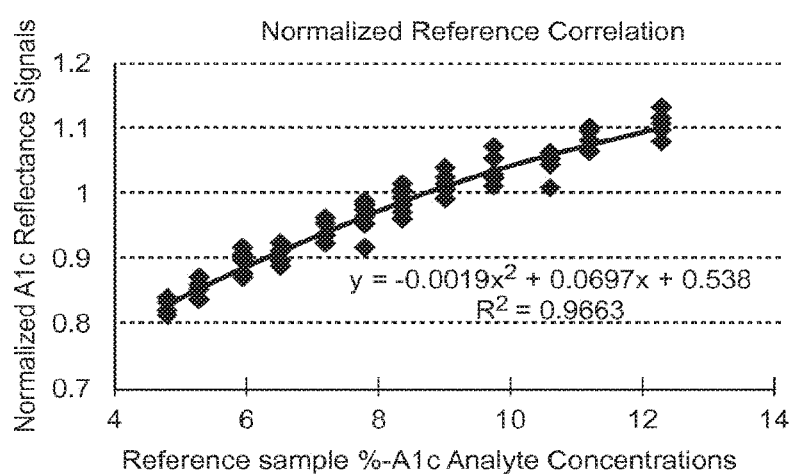
FIG. 2F provides an example of the determination of a normalized reference correlation from combining the normalized analyte responsive output signal values of FIG. 2E.
Figure 2G:
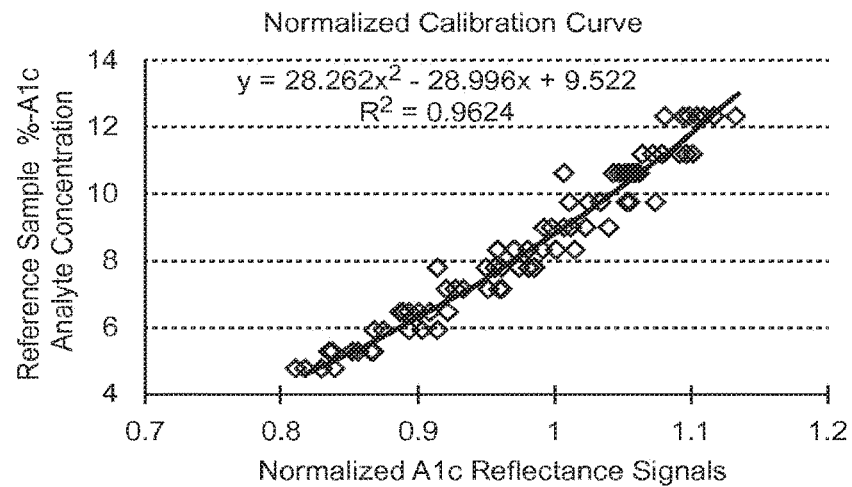
FIG. 2G provides another example of the determination of a normalized reference correlation from the normalized analyte responsive output signal values of FIG. 2E.
Figure 4E:
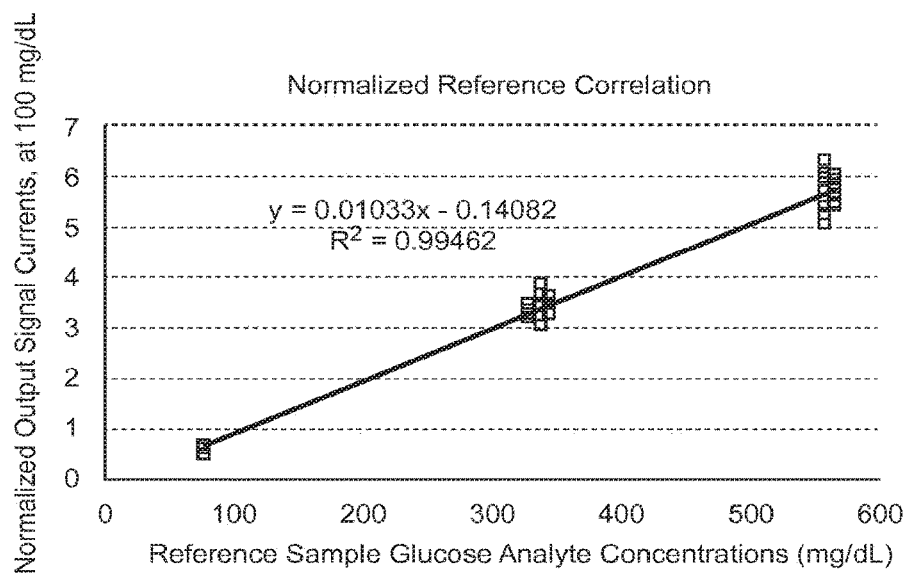
FIG. 4E provides an example of the determination of a normalized reference correlation from the normalized analyte responsive output signal values of FIG. 4D.

For example in MS Excel version 2010, the Linear Trendline Option accessible through the Trendline Layout Chart Tool may be selected to perform linear analysis, while the Polynomial Trendline Option may be chosen to perform a non-linear polynomial analysis. Other regression techniques may be used to determine the normalized reference correlation 172. FIG. 2F, as addressed further below, provides an example of the normalized reference correlation determination 170 in an A1c analysis system. FIG. 2G represents the determined normalized reference correlation 172 expressed as a normalized calibration curve. FIG. 4E, as addressed further below, provides an example of the normalized reference correlation determination 170 in a glucose analysis system.

When linear regression is used, the normalized reference correlation 172 will be in the form of $Y=mX+b$, where m is slope and b is an intercept of the regression line. When non-linear regression is used, such as a polynomial, the normalized reference correlation 172 may be in a form of $Y=b_2*X^2+b_1*X+b_0$, and the like, where $b_2$, $b_1$ and $b_0$ are the coefficients of the polynomial. The normalized reference correlation 172 is preferably stored in the measurement device as a portion of the calibration information for later use during the analysis of a sample. In the measurement device, Y is the normalized analyte responsive output signal value determined during the analysis, and X is the analyte concentration of the sample as determined from the normalized reference correlation 172. As discussed further below, for the linear normalized reference correlation, an X value (the sample analyte concentration) may be solved for when inputting a Y value (a value of the normalized output signal) into the equation. For a normalized reference correlation in the form of a $2^{nd}$ order polynomial, the normalized reference correlation 172 may be expressed in the form of a normalized calibration curve as $X=c_2*Y+c_1*Y+c_0$ where $c_2$, $c_1$ and $c_0$ are coefficients for the equation. A normalized output signal input to this relationship will generate an analyte concentration.

FIG. 1B represents an optional calibration method 102 that considers a second extraneous stimulus with the normalized calibration information. Calibration method 102 provides normalized calibration information from the second extraneous stimulus for incorporation into a measurement device of a biosensor system with a reduced stimulus effect. Preferably, the calibration method 102 also is performed during factory calibration of the measurement device. The calibration method 102 also may be performed in a laboratory or similar setting. The calibration method may be performed by the measurement device, one or more analytical devices such as a computer, or a combination of the measurement and analytical devices. Calibration method 102 combines with calibration method 100 to provide normalized calibration information from a first extraneous stimulus and a second extraneous stimulus. Thus, FIG. 1A and FIG. 1B may be combined when determining calibration information for the measurement device of the biosensor system.

If a second extraneous stimulus adversely affecting the analyte responsive output signals is considered, such as the hematocrit concentration of the sample when the first extraneous stimulus is temperature, at least two second quantified extraneous stimulus values 134 may be determined in accord with the extraneous stimulus quantification 130. FIG. 5D and FIG. 5E, as addressed further below, provide an example of the determination of second quantified extraneous stimulus values 134 in a glucose analysis system.

Then a second normalizing relationship 147 may be determined in accord with the normalizing relationship determination 140, but where the second normalizing relationship 147 is determined between the normalized analyte responsive output signals 162 and the second quantified extraneous stimulus values 134 at a single selected sample analyte concentration. The second normalizing relationship 147 is preferably stored in the measurement device as a portion of the calibration information. FIG. 5F, as addressed further below, provides an example of the determination of a second normalizing relationship 147 in a glucose analysis system.

In the case of the second extraneous stimulus, a second normalizing value determination 155 is performed. A second normalizing value 157 is determined from the second normalizing relationship 147 by inputting the second quantified extraneous stimulus values 134 into the second normalizing relationship 147 and solving for the second normalizing value 157.

In the case of the second extraneous stimulus, a second normalized output signal determination 165 is performed. Second normalized analyte responsive output signals 167 are determined by dividing the normalized analyte responsive output signals 162 by the second normalizing value 157. FIG. 5G, as addressed further below, provides an example of determining second normalized analyte responsive output signals 167 in a glucose analysis system.

In the case of the second extraneous stimulus, a second normalized reference correlation determination 175 is performed. A second normalized reference correlation 177 is determined between the second normalized analyte responsive output signals 167 and the reference sample analyte concentrations 124 by a regression technique, as previously described. FIG. 5H, as addressed further below, provides an example of determining a second normalized reference correlation 177 in a glucose analysis system.

The second normalized reference correlation 177 is preferably stored in the measurement device as a portion of the calibration information. In this case, the normalized reference correlation 172 does not need to be stored in the measurement device and is preferably not used during the analysis. Similarly, three or more extraneous stimulus may be considered by the calibration information, where each extraneous stimulus is represented by an individual normalizing relationship stored in the measurement device in addition to a single normalized reference correlation prepared for the combined extraneous stimulus represented by the individual normalizing relationships.

FIG. 1C represents an analysis method 200 of determining the analyte concentration of a sample with a reduced extraneous stimulus effect using a normalized reference correlation. The analysis method 200 is preferably performed when a user activates a measurement device of a biosensor system to analyze a sample, such as blood. Preferably, the sample is blood including red blood cells. Optical and/or electrochemical methods may be used to analyze the sample.

In analysis analyte responsive output signal measurement 220, one or more analyte responsive output signal values 222 are measured from the sample, where the analyte responsive output signal values are affected by one or more extraneous stimulus, such as a physical characteristic, an environmental aspect, and/or a manufacturing variation, that results in an error being incorporated into the analyte responsive output signal values. The analyte responsive output signal values 222 are measured from one or more output signals generated from the sample using optical and/or electrochemical methods, such as gated amperometry, gated voltammetry, or the like.

In analysis extraneous stimulus quantification 230, one or more extraneous stimulus responsive output signals are measured. One or more quantified extraneous stimulus values are determined in response to the extraneous stimulus responsive output signals. From method 100, a single or first quantified extraneous stimulus value 232 may be determined in response to a first extraneous stimulus. Methods 100 and 102 may be combined to determine a first quantified extraneous stimulus value 232 in response to a first extraneous stimulus and a second quantified extraneous stimulus value 234 in response to a second extraneous stimulus. Other quantified extraneous stimulus values may be determined. Thus, a quantified extraneous stimulus value is determined for each extraneous stimulus addressed by the calibration information. The quantified extraneous stimulus responsive output signals are measured from one or more output signals generated from the sample using optical and/or electrochemical methods, such as gated amperometry, gated voltammetry, or the like In analysis normalizing value determination 250, one or more previously determined normalizing relationships are used to determine one or more normalizing values. Examples of previously determined normalizing relationships are the previously described normalizing relationship 142 and the previously described second normalizing relationship 147. For example, one or more of the analyte responsive output signal values 222 and the quantified extraneous stimulus value 232 are input into the normalizing relationship 142. Similarly, one or more of the analyte responsive output signal values 222 and the quantified extraneous stimulus value 234 are input into the second normalizing relationship 147. In this way, extraneous stimulus value 232 or 234 may be input to the normalizing relationship 142 or 147 to determine the normalizing value. Thus, one or more analyte responsive output signal values and one or more quantified extraneous stimulus values are input into one or more normalizing relationships to determine one or more normalizing values.

In normalized analyte responsive output signal determination 260, at least one normalized analyte responsive output signal value is determined in response to the one or more analyte responsive output signal values and one or more normalizing values. The one or more analyte responsive output signal values 222 are divided by the normalizing value to determine one or more normalized analyte responsive output signal values 262 (in the case of one external stimulus) or 267 (in the case of two external stimulus). Preferably, one analyte responsive output signal value is used to determine one normalized analyte responsive output signal value.

In analysis analyte concentration determination 280, one or more analyte concentrations in the sample are determined in response to one or more normalized reference correlations and one or more normalized analyte responsive output signals. Preferably, a previously determined normalized reference correlation, such as the previously described normalized reference correlation 172 or 177, transforms the one or more normalized analyte responsive output signal values 262 or 267 into an analyte concentration of the sample 282. Preferably, the previously described normalized reference correlation 172 or 177 is transforms one normalized analyte responsive output signal value into an analyte concentration of the sample. When two or more analyte concentrations of the sample are determined, the analyte concentrations may be averaged to provide an average analyte concentration of the sample.

In 290, the analyte concentration of the sample 282 may be displayed, stored for future reference, compensated, and/or used for additional calculations.

Thus, in the analysis method 200 the normalized reference correlation 172 or 177 is incorporated into the measurement device and used similarly to how a conventional reference correlation would be used to translate primary output signal values into determined analyte concentrations of the sample. Except that in the analysis method 200, instead of primary output signal values being transformed by the reference correlation 122, the normalized analyte responsive output signal value/s 262 or 267 are transformed by the normalized reference correlation 172 or 177, respectively, to provide the analyte concentration of the sample with reduced effect from one or more extraneous stimulus.

An example of the calibration method 100 for determining calibration information with a reduced extraneous stimulus effect for incorporation into the measurement device using this normalization process for calibration is shown in FIGS. 2A-2H for an A1c analysis system. In this example, the sample is blood; the sample analyte is the A1c in the blood samples and the sample analyte concentration is the sample %-A1c. The A1c is the primary stimulus while the THb is the extraneous stimulus. The numerical values calculated throughout FIGS. 2A-2H would be different for a different analysis system or even a different A1c analysis system. This method is represented with the plots in FIG. 2B through FIG. 2H.

FIG. 2A shows A1c reflectance signals recorded from the Zone 1 detector/s of the measurement device versus reference sample analyte concentrations (%-A1c) at four THb concentrations (85 mg/mL, 125 mg/mL, 175 mg/mL, and 230 mg/mL). The %-A1c measurement was repeated twice for each reference sample of blood including a known concentration of A1c. Because the A1c reflectance signals measured from the Zone 1 detector/s of the measurement device are THb dependent, the A1c reflectance signals are spread out for the same %-A1c reference sample analyte concentration. Thus, even though the actual A1c concentration was identical for a set of reference samples, the measured A1c reflectance signals measured from the Zone 1 detector/s for the reference sample set was different due to the THb extraneous stimulus. The equation shown in the figure represents a conventional reference correlation for this analysis where the output signals from the measurement device are directly translated into analyte concentrations by this equation. Note the relatively low $R^2$ correlation of 0.6272 between the determined reference correlation ($Y=0.0006x^2+0.0263x+0.2239$) and the output signals from the reference samples.

FIG. 2B shows the comparatively constant THb output signals at the four THb reference sample concentrations (85 mg/mL, 125 mg/mL, 175 mg/mL, and 230 mg/mL) as determined from the Zone 2 detectors of the measurement device. Thus, for each THb concentration, an average signal value of the extraneous stimulus THb was determined. For example, a quantified extraneous stimulus signal value of ~0.76 was determined from FIG. 1B at the 85 mg/mL THb sample concentration by averaging. Methods other than averaging may be used to quantify the extraneous stimulus from the secondary output signals.

FIG. 2C shows the individual A1c reflectance signals recorded from the Zone 1 detector/s of the measurement device separated for the four different THb concentrations in blood samples. This allows a single sample analyte concentration to be selected from which synthesized extraneous stimulus responsive output signal values may be determined from the primary output signals. In this example, linear regression lines were determined at each of the 4 THb sample concentrations using the general relationship ($R_{A1c}$=Slope*%-A1c+Int, where $R_{A1c}$ is the output signal from the measurement device, Slope and Int are the slope and intercept, respectively of the linear regression lines at each THb sample concentration, and %-A1c is the sample analyte concentration). Other regression techniques may be used.

The regression equations determined at the 85 THb mg/mL and 230 THb mg/mL are shown on the figure, but regression equations at 127 and 175 mg/mL THb also were determined. In this example, the single selected sample analyte concentration of 9%-A1c was selected to determine the synthesized extraneous stimulus responsive output signal values from the primary output signals. Thus, in this example, the reference sample analyte concentration of 9% provided an ~0.36 A1c synthesized extraneous stimulus responsive output signal value for the 85 mg/mL THb samples from the 85 mg/mL THb regression line and an ~0.44 A1c synthesized extraneous stimulus responsive output signal value for the 230 mg/mL THb samples from the 230 mg/mL THb regression line.

Synthesized extraneous stimulus responsive output signal values can be determined in other ways than determining regression lines and "back determining" a primary output signal value from a selected reference sample analyte concentration. For example, synthesized extraneous stimulus responsive output signal values may be selected from the measured primary output signal values at one reference sample %-A1c concentration for all four THb levels. A single THb reflectance signal measured concurrently is paired with the A1c reflectance signal to form the four pairs of A1c and THb data and to construct the plot of A1c reflectance vs. THb reflectance, which will also lead to the normalizing relationship.

While the single selected sample analyte concentration of 9%-A1c was chosen in FIG. 2C, reference sample analyte concentrations of 6 through 11%-A1c also may preferably be selected. Thus, the single selected sample analyte concentration at which to determine the synthesized extraneous stimulus responsive output signal values is preferably near the middle of the range of reference sample analyte concentrations, but can be on either side of the middle to provide the desired measurement performance to the analysis system.

Table A, below, shows the data pairs collected from averaging the THb signals at the same level of THb and the corresponding synthesized THb responsive output signals calculated at a single %-A1c concentration (in this example 9% A1c) through the above general regression relationship ($R_{A1c}$=Slope*%-A1c+Int) as in FIG. 2C.

TABLE A

Synthesized and Average THb Signal Values

| THb (mg/mL) | 85 | 125 | 175 | 230 |
|---|---|---|---|---|
| THb/70 (mg/mL)* | 1.214 | 1.786 | 2.5 | 3.286 |
| Quantified (Avg.) secondary output signal from FIG. 2B | 0.7572 | 0.7302 | 0.7069 | 0.6796 |
| Synthesized THb Responsive Output Signal Values at A1c Conc. (9) from FIG. 2C | 0.3659 | 0.3964 | 0.4183 | 0.4400 |

*The samples were diluted to obtain signals appropriate for the detectors.

FIG. 2D is a correlation plot of these four pairs of data where the synthesized extraneous stimulus responsive output signals extracted from the A1c output signal in Y-axis is plotted against the THb signals (secondary output signals) in the X-axis, the extraneous stimulus. FIG. 2D also provides an example of determining the normalization relationship 140, which establishes the correlation between the synthesized extraneous stimulus responsive output signals at a single A1c concentration and the secondary output signals responsive to the sample THb concentrations.

A regression technique, in this case polynomial ($a_2$*THb$^2$+$a_1$*THb+$a_0$, where $a_2$, $a_1$ and $a_0$ are the coefficients of the $2^{nd}$ order polynomial normalization function from curve-fitting and THb is the quantified extraneous stimulus value for THb), was then used to determine the normalizing relationship 142 between the synthesized extraneous stimulus responsive output signals at a single selected sample analyte concentration and the quantified extraneous stimulus signals. The specific normalization relationship for the A1c analysis data from this example is shown in FIG. 2D as Y=3.34X$^2$+3.85X−0.63, thus showing the specific $2^{nd}$ order polynomial coefficients for this example, where Y is the calculated synthesized extraneous stimulus responsive output signal responsive to the extraneous stimulus at a single selected analyte concentration, and X is the quantified extraneous stimulus signals/values. A different analysis would have different regression coefficients. When a value of X (the quantified extraneous stimulus signal value) is entered into the $2^{nd}$ order polynomial, a value of Y is generated through this normalizing relationship, which is the normalizing value (NV).

FIG. 2E provides an example of the determination of normalized analyte responsive output signals 162 using the normalizing value. Thus, the A1c reflectance signals from FIG. 2C are converted to normalized primary output signal values using the normalization relationship of FIG. 2D and the normalizing value. The determination of normalized analyte responsive output signals from the normalizing relationship and the normalizing value may be represented by the relationship $NR_{A1c}=R_{A1c}/NV_{A1c}$, where $NR_{A1c}$ are the THb normalized analyte responsive output signals, $R_{A1c}$ are the A1c reflectance signals from the measurement device, and $NV_{A1c}$ is the normalizing value.

Preferably, the determination of normalized analyte responsive output signals is performed for all or the majority of the analyte responsive output signal to determine the calibration information. However, a subset of the analyte responsive output signal may be used depending on the analysis system. Thus, in FIG. 2E, the analyte responsive output signal values from FIG. 2C were normalized by being divided with the corresponding normalizing values through the normalizing relationship determined in FIG. 2D using the normalizing value from FIG. 2F to provide the normalized analyte responsive output signal values shown in FIG. 2E, which are then combined into FIG. 2F.

FIG. 2F provides an example of the determination of a normalized reference correlation from the normalized analyte responsive output signals of FIG. 2F. $NR_{A1c}$ was plotted vs. the reference sample analyte concentrations (%-A1c) and curve-fitted by a regression technique to provide the normalized reference correlation. A regression technique, in this case $2^{nd}$ order polynomial ($a_2$*%-A1c$^2$+$a_1$*%-A1c+$a_0$, where $a_2$, $a_1$, and $a_0$ are coefficients of the polynomial and %-A1c is the analyte concentration of the reference samples), was used to determine the normalized reference correlation.

The specific normalized reference correlation for the A1c analysis data from this example is shown in FIG. 2F as $y=-0.1119X^2+0.0697X+0.538$, thus showing the specific $2^{nd}$ order polynomial coefficients for this example. A different analysis would have different coefficients. Also shown in FIG. 2F is the $R^2=0.9663$, showing the excellent agreement between the normalized primary output signals and the reference sample analyte concentrations for %-A1c. In this determination of the normalized reference correlation, the normalized primary output signal was the dependent variable, while the reference sample analyte concentrations for %-A1c was the independent variable for the regression. Thus, this normalized reference correlation may be thought of as outputting the normalized analyte responsive output signal values from the reference sample analyte concentrations for %-A1c.

FIG. 2G provides another example of the determination of a normalized reference correlation from the normalized analyte responsive output signal values of FIG. 2E. In FIG. 2G, the normalized analyte responsive output signal was the independent variable, while the reference sample analyte concentration for %-A1c was the dependent variable for the regression. Thus, the horizontal x and vertical y axes are reversed. In this example, the determined normalized reference correlation was $y=28.26X^2-28.996X+0.522$ and the $R^2$ correlation was 0.962, again showing the excellent agreement between the normalized analyte responsive output signals and the reference sample analyte concentrations for %-A1c. A different analysis would have different regression coefficients. Thus, this normalized reference correlation may be thought of as outputting the reference sample analyte concentrations for %-A1c from the normalized analyte responsive output signal values.

A normalized reference correlation expressed in this way may be considered a "normalized calibration curve". Such a normalized calibration curve providing sample analyte concentrations is preferred for storage in the measurement device for use during the analysis 200 as the biosensor system determines an analyte concentration from the primary output signal, and not the reverse as would be obtained from the normalized reference correlation of FIG. 2F. Thus, when a value of X (the normalized output signal) is entered into the $2^{nd}$ order polynomial equation, a value of Y (the analyte concentration) is obtained.

Figure 2H:
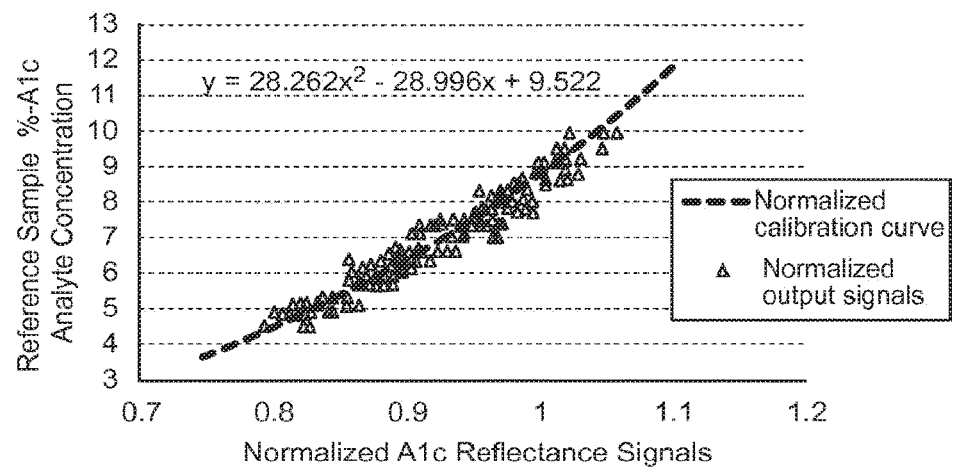
FIG. 2H compares the normalized analyte responsive output signals to the normalized reference correlation in the form of a normalized calibration curve from FIG. 2G by superimposing the normalized analyte responsive output signal values on the curve.

FIG. 2H compares the normalized analyte responsive output signals to the normalized reference correlation in the form of a normalized calibration curve from FIG. 2G by superimposing the normalized analyte responsive output signal values on the curve. Another point of interest is the comparison of the $R^2$ correlation value of 0.6272 determined in FIG. 2A for the conventional reference correlation and $R^2$ correlation value of 0.9663 determined in FIG. 2F for the normalized reference correlation. The approximately 54% (0.9663−0.6272/0.6272*100) improvement in the normalized reference correlation establishes the superiority of the normalized output signal values/normalized reference correlation in determining analyte sample concentrations in comparison to the conventional measured output signal values/reference correlation.

The resultant calibration information including the normalizing relationship and the normalized reference correlation may be stored in the measurement device in the form of a look-up table, one or more equations, and the like. Other relationships also may be stored in the measurement device. The calibration information is used by the processor of the measurement device during sample analysis to determine the analyte concentration of the sample.

In a measurement device with one primary output signal, the above techniques may be used to determine calibration information for the one primary output signal. However, for measurement devices with more than one primary output signal, calibration information may be determined for each primary output signal, and the analyte concentrations determined from the different calibration information combined. For example, in an A1c measurement device having more than one detector for Zone 1 with which to determine the primary stimulus, calibration information may be determined for each detector channel and then the final analyte concentration determined by averaging the initial analyte concentration determined from each detector channel.

Alternatively, for measurement devices with more than one primary output signal of the same primary stimulus, the output signals initially may be combined and calibration information determined for the combined signal. The independent output signals may then be transformed into analyte concentrations using the combined calibration information to provide initial analyte concentrations that are then combined to provide the analyte concentration of the sample, or the combined output signals may be transformed by the calibration information determined for the combined signal to provide the analyte concentration of the sample. For example, in an A1c measurement device having more than one detector for Zone 1, the output signals from both detectors may be averaged and calibration information determined for the averaged output signals from both detectors. Then, the averaged output signal may be transformed into the analyte concentration of the sample by the calibration information determined from the averaged output signal or the output signal from both channels transformed by the calibration information determined from the averaged output signal to provide two initial analyte concentrations, which are then averaged to provide the final analyte concentration of the sample.

The examples described with regard to FIGS. 3A-3E show the benefit of determining independent calibration information for each of two individual detector channels of a measurement device, where each of the two output signal channels includes both A1c and THb responsive information. The numerical values calculated throughout FIGS. 3A-3E would be different for a different analysis system or even a different A1c analysis system.

Figure 3A:
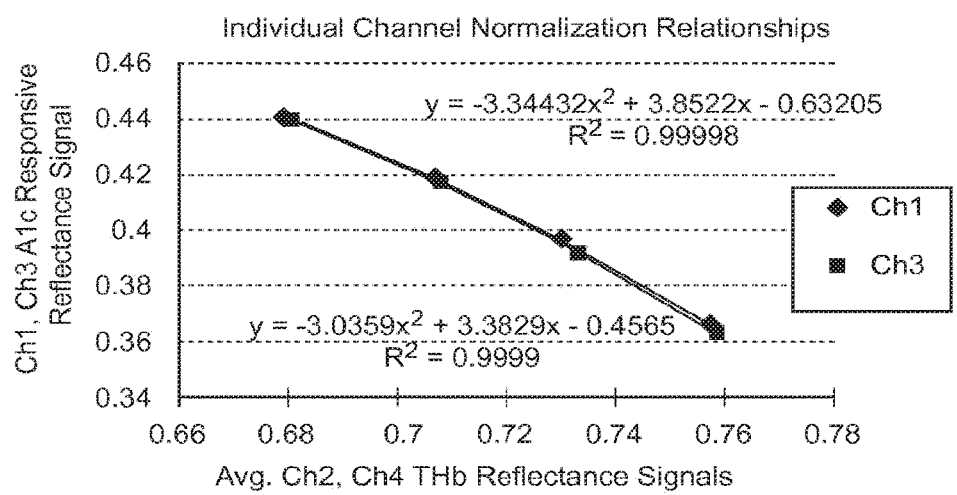
FIG. 3A represents the normalization relationships for both channels of an A1c measurement device having two detection channels.

FIG. 3A represents the normalization relationships for both channels of an A1c measurement device having two detection channels. Thus, for this example, FIG. 3A shows the two separate normalizing relationships for the primary output signals from the Zone 1 channel one detector (Ch1) and the secondary output signals from the Zone 2 channel two detector (Ch2); and for the primary output signals from the Zone 1 channel three detector (Ch3) and the secondary output signals from the Zone 2 channel four detector (Ch4).

Thus, Ch1 and Ch3 provide A1c responsive output signals, while Ch2 and Ch4 provide THb responsive output signals.

Figure 3B:
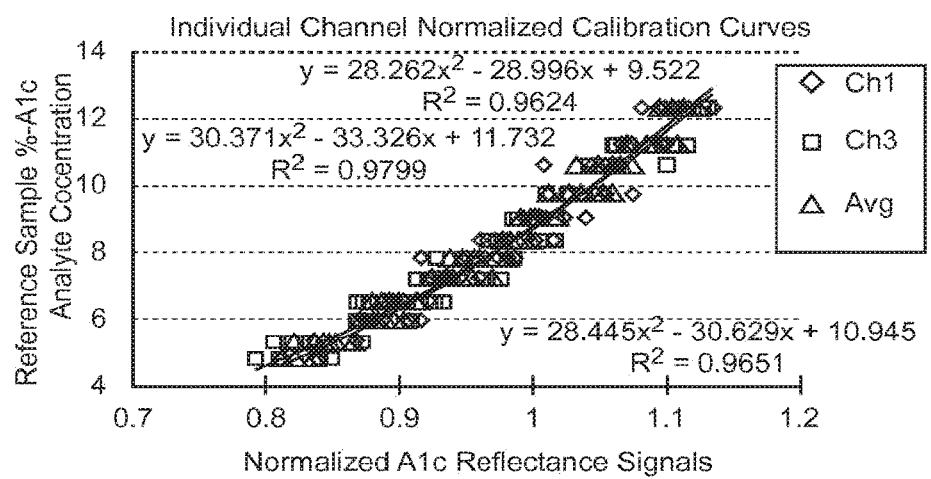
FIG. 3B represents the individual normalized calibration curves for Ch1 and Ch3 of the A1c measurement device.

FIG. 3B represents the individual normalized calibration curves for Ch1 and Ch3 of the A1c measurement device. Also plotted on the figure are the normalized output signals determined from Ch1/Ch2, the normalized output signals determined from Ch3/Ch4, and the average of these normalized output signals. A polynomial regression technique was used to determine the normalized reference correlations in the form of normalized calibration curves, as previously described.

Figure 3C:
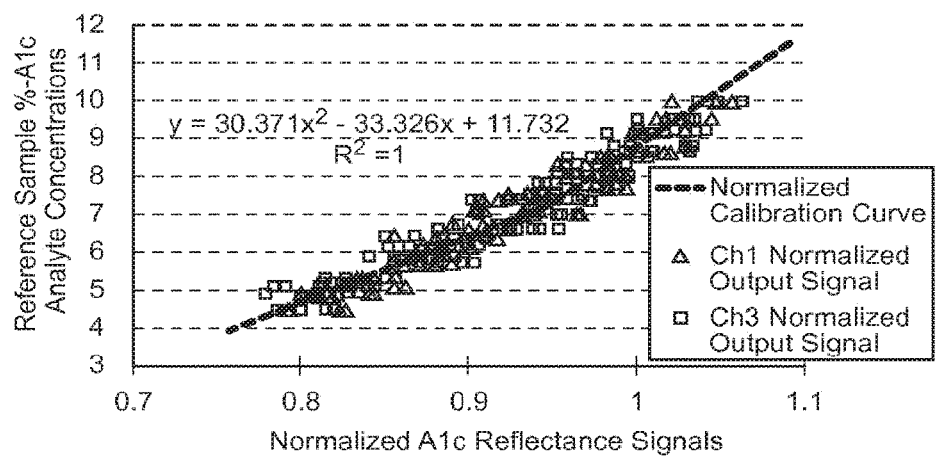
FIG. 3C shows the normalized A1c reflectance signals from the two individual channels (Ch1 & Ch3) for the reference samples.

FIG. 3C shows the normalized A1c reflectance signals from the two individual channels (Ch1 & Ch3) for the reference samples. Averaging may be performed for the two initial %-A1c concentrations to provide the final A1c concentration. The mean and percent bias standard deviation (SD) values in Table 1 and in Table 2 below show the separate individual channels results, as well as the average A1c results for the calibration and measurement device sample analyses, respectively. For both the calibration, using reference samples, and analyses, performed with the measurement device using the calibration information, the averaged determined analyte concentrations are improved over the individual channel results. From Table 2, the Ch1 bias standard deviation was reduced by nearly nine percent (8.8%) (5.58−5.09/5.58*100), while the Ch2 bias standard deviation was reduced by over 18% (18.3%) (6.23−5.09/6.23*100) for the average. Thus, the bias standard deviation was reduced by an average of greater than 10% (13.5%) (8.8+18.3/2) for the averaged determined analyte concentrations.

TABLE 1

| Calibration | | | |
|---|---|---|---|
| | %-bias1 | %-bias3 | %-bias_Avg |
| Mean | 0.274 | 0.295 | 0.156 |
| SD | 5.25 | 5.52 | 3.97 |

TABLE 2

| Analysis | | | |
|---|---|---|---|
| | %-bias1 | %-bias3 | %-bias_Avg |
| Mean | 0.055 | 0.184 | 0.120 |
| SD | 5.58 | 6.23 | 5.09 |

Figure 3D:
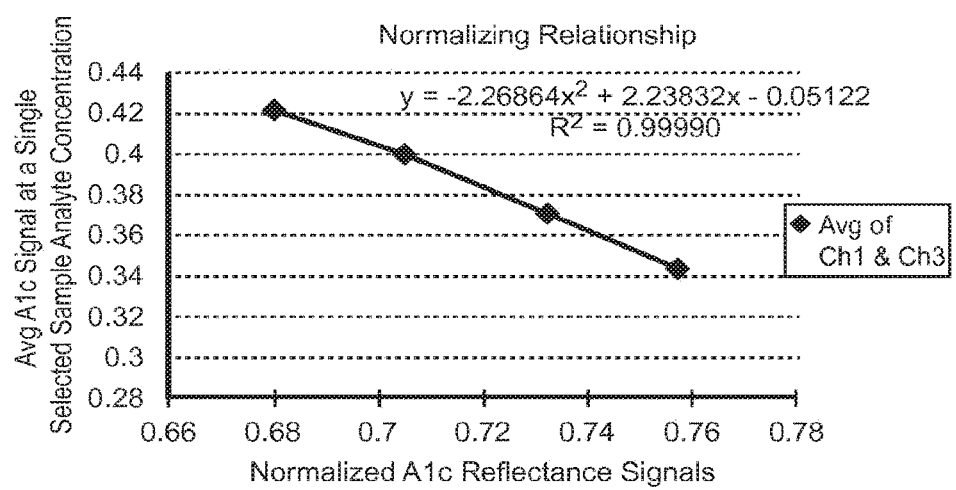
FIG. 3D shows the normalizing relationship determined by first averaging the A1c reflectance output signals from Ch1 and Ch3 of the measurement device.
Figure 3E:
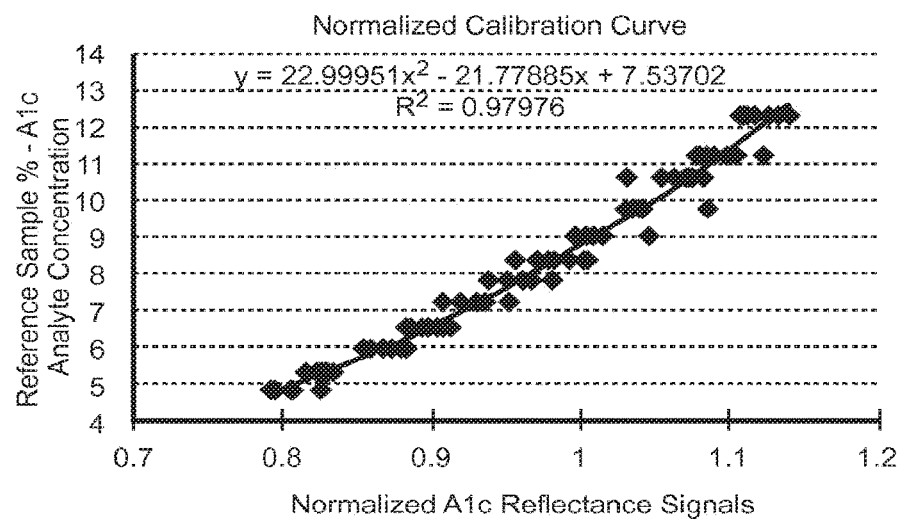
FIG. 3E shows the normalized reference correlation in the form of a normalized calibration curve determined for the averaged A1c reflectance signals from Ch1 and Ch3 of the measurement device.

In addition to determining calibration information for each channel, and then combining the intermediate sample concentrations determined for each channel, the output signals from each channel may be first combined and then used to determine calibration information for the combined signal. FIG. 3D shows the normalizing relationship determined by first averaging the A1c reflectance output signals from Ch1 and Ch3 of the measurement device. Thus, the same output signals used to determine the two normalizing relationships represented in FIG. 3A were first averaged. FIG. 3E shows the normalized reference correlation in the form of a normalized calibration curve determined for the averaged A1c reflectance signals from Ch1 and Ch3 of the measurement device. Output signals from each channel of the measurement device can then be converted to initial analyte concentrations with this calibration information and the initial analyte concentrations averaged to determine a final sample analyte concentration.

An example of the calibration method 100 for determining calibration information with a reduced extraneous stimulus effect for temperature on the primary output signal from an electrochemical glucose analysis system is shown in FIGS. 4A-4F. In this example, the sample is the blood and the sample analyte is the glucose (the primary stimulus). The sample analyte concentration is the sample glucose concentration and the extraneous stimulus are temperature and hematocrit.

For the temperature effect, the currents measured by the measurement device from reference samples at 40% Hct (the %-Hct at which the conventional reference correlation relating output currents and reference sample analyte concentrations was determined) and at different temperatures were normalized. In this type of glucose system, the working and counter electrodes provide the primary output signal while the temperature sensor provides the secondary output signal. This process is represented with the plots in FIG. 4A through FIG. 4F. The numerical values calculated throughout FIGS. 4A-4F would be different for a different analysis system or even a different glucose analysis system.

FIG. 4A plots the currents obtained from the measurement device versus reference sample analyte concentrations for glucose at different temperatures and 40% Hct. The currents become more widely spread due to changes in temperature at higher sample glucose concentrations. While the currents determined by the measurement device from reference samples including ~80 mg/dL of glucose in blood were closely grouped around ~75 nA, the currents determined by the measurement device from reference samples including ~320 mg/dL and ~580 mg/dL of glucose were widely spaced. In fact, as shown in FIG. 4A a linear regression line determined from these currents showed an $R^2$ correlation of only 0.6. This figure may be thought of as showing the effect of an extraneous stimulus on analyte responsive output signals as previously observed in FIG. 2C. In FIG. 2C the extraneous stimulus was sample THb, while in FIG. 4A it was temperature.

FIG. 4B separates these primary output signal currents by the temperature at which they were recorded. Thus, temperature is the extraneous stimulus that adversely affects the analyte responsive output signal currents from the measurement device, even though the analyte concentrations of the reference samples are identical at each temperature. In this example, linear regression lines were determined at each of the 5 temperatures using the general relationship $i_G = \text{Slope} * G_{Ref} + \text{Int}$, where $i_G$ is the glucose responsive current from the measurement device and $G_{Ref}$ is the reference sample analyte concentration for glucose from which to determine the synthesized extraneous stimulus responsive output signal values. Other techniques may be used to determine the synthesized extraneous stimulus responsive output signal values.

In FIG. 4B, two sample glucose concentrations of 100 and 500 mg/dL were selected at which to determine the synthesized extraneous stimulus responsive output signal values at their corresponding temperatures. Thus, unlike in the A1c system where the single selected sample analyte concentration of 9% was selected, this example shows that synthesized extraneous stimulus responsive output signal values may be determined at more than one single selected sample analyte concentration. Single selected sample analyte concentrations other than 100 and 500 mg/dL may be used.

Table 3, below, provides the synthesized extraneous stimulus responsive output signal values obtained for each temperature at 100 and 500 mg/dL glucose sample analyte concentration from the individual regression lines by using the regression equations similar to that previously described with regard to the A1c example ($i_G$=Slope*$G_{Ref}$+Int). The temperatures values in the table are averages from all the measured temperatures when performing the analysis of the reference samples at the target temperatures. Thus, Table 3 forms two sets of pairs at the selected single glucose concentration of 100 or 500 mg/dL, each set containing seven pairs of output signals-temperatures data.

TABLE 3

Synthesized Output Signal Values

| | Avg. Temp. C. | | | | | | |
|---|---|---|---|---|---|---|---|
| | 6.0 | 10.9 | 15.9 | 22.0 | 30.4 | 35.1 | 40.0 |
| 500 mg/dL | 205.78 | 283.53 | 373.96 | 462.61 | 639.89 | 705.54 | 809.11 |
| 100 mg/dL | 41.16 | 56.71 | 74.79 | 92.52 | 127.98 | 141.11 | 161.82 |

Thus, FIG. 4B separates the output currents from the measurement device by temperature, as opposed to THb sample concentration as described in FIG. 2C. Only five correlation lines were plotted for five of the seven temperatures tested, in order not to crowd the plot.

FIG. 4C shows the correlations between the synthesized extraneous stimulus responsive output signals obtained at two separate single glucose concentration of 100 and 500 mg/dL versus the quantified extraneous stimulus (temperatures) to determine the normalization relationships. FIG. 4C also provides an example of determining the normalization relationship 140, which considers temperature for normalization of the analyte responsive output signals. The vertical Y-axis of FIG. 4C shows the extraneous stimulus responsive values as synthesized from the regression lines of FIG. 4B and determined at the single selected sample analyte concentrations of 100 and 500 mg/dL glucose for the five temperatures. The horizontal X-axis of FIG. 4C shows the average value determined at each target temperature for the extraneous stimulus temperature.

A regression technique, in this case polynomial ($a_2$*$T^2$+$a_1$*T+$a_0$, where $a_2$, $a_1$ and $a_0$ are the coefficients of the $2^{nd}$ order polynomial normalization function from curve-fitting and T is the quantified extraneous stimulus value for temperature), was then used to determine the normalizing relationship 142 between the synthesized extraneous stimulus responsive output signals at a single selected sample analyte concentration and the quantified extraneous stimulus signals. The specific normalization relationship for the 100 and 500 mg/dL glucose analysis data from this example is shown in FIG. 4C as y=0.0104$X^2$+3.0646x+22.366 (100 mg/dL) and y=0.05214$X^2$+15.3228x+111.832 (500 mg/dL), thus showing the specific $2^{nd}$ order polynomial coefficients for this example, where Y is the calculated synthesized extraneous responsive output signal responsive to the extraneous stimulus signal at a single selected analyte concentration, and X is the quantified extraneous stimulus signals/values. A different analysis would have different coefficients. When a value of X (the quantified extraneous stimulus signal value) is entered into the $2^{nd}$ order polynomial, a value of Y is generated through this normalizing relationship, which is the normalizing value (NV). This figure may be thought of similarly as to FIG. 2D; however, in this example, normalizing values may be determined at two reference sample analyte concentrations.

FIG. 4D provides an example of the determination of normalized analyte responsive output signals 162 from the normalizing value at 100 mg/dL. Thus, the analyte responsive output signals from the vertical y-axis of FIG. 4B were converted to normalized primary output signal values by dividing the analyte responsive output signals with their corresponding normalizing values obtained from the normalization relationship of FIG. 4C. The determination of the normalized analyte responsive output signals from the normalizing relationship and the normalizing value may be represented by the relationship $Ni_G = i_{measured}/NV_{Temp}$, where $Ni_G$ are the temperature normalized analyte responsive output signals, $i_{measured}$ are the glucose responsive currents from the measurement device, and $NV_{Temp}$ is the normalizing value determined from temperature normalization. Thus, the five individual lines of FIG. 4B for the different temperatures collapsed into a group of closely packed lines as represented in FIG. 4D. As previously discussed, preferably, the determination of normalized analyte responsive output signals is performed for all or the majority of the analyte responsive output signal to determine the calibration information.

FIG. 4E provides an example of the determination of a normalized reference correlation from the normalized analyte responsive output signal values of FIG. 4D. $Ni_G$ was plotted vs. the reference sample analyte concentrations and curve-fitted by a regression technique to provide the normalized reference correlation. A regression technique, in this case linear (Y=Slope*X+Int), was used to determine the normalized reference correlation, where during the analysis 200 Y is the normalized primary output signal determined by the measurement device and X is the reference analyte concentration of the sample. Thus, when a Y value (the normalized output signal) is entered into the linear regression equation, an X value (the analyte concentration) is obtained by solving the equation.

The specific normalized reference correlation for the glucose analysis data from this example is shown in FIG. 4E as Y=0.01033X−0.14082, thus showing the specific linear coefficients for this example. A different analysis would have different coefficients. Also shown in FIG. 4E is the $R^2$=0.9946, showing the excellent agreement between the normalized primary output signals and the reference sample analyte concentrations. Thus, this normalized reference correlation may be thought of as providing determined sample analyte concentrations for glucose from the normalized analyte responsive output signal values.

For the temperatures measured (6.0° C., 10.9° C., 15.9° C., 22.0° C., 30.4° C., 35.1° C., and 40.0° C.), the average temperatures, the regression slope obtained at each temperature using a conventional reference correlation, and the regression slope obtained at each temperature using the normalized reference correlation at the 100 mg/dL glucose reference sample analyte concentration are tabulated in Table 4, below.

TABLE 4

Summary of Normalization for Temperature Stimulus

| Temp ° C. | Conventional Reference Correlation Slopes | Normalized Reference Correlation Slopes |
|---|---|---|
| 6.0 | 0.412 | 0.0103 |
| 10.9 | 0.567 | 0.0099 |
| 15.9 | 0.748 | 0.0101 |
| 22.0 | 0.925 | 0.0097 |
| 30.4 | 1.280 | 0.0102 |
| 35.1 | 1.411 | 0.0099 |
| 40.0 | 1.618 | 0.0100 |
| Mean slope | 0.9944 | 0.0100147 |
| SD, slope | 0.4532 | 0.00023014 |
| %-CV | 45.6 | 2.3 |

The improvement in measurement performance may be better appreciated by looking at the mean response slopes and the %-CV of the slopes before and after normalization. The %-CV of the response slopes determined with primary output signals from the measurement device and a conventional reference correlation was 45.6%. In contrast, the %-CV of the response slopes determined with the described normalized primary output signals and normalized reference correlation was reduced to 2.3%, an approximate 95% reduction (45.6−2.3/45.6*100). This reduction is graphically represented when the normalized output signal currents are transformed into sample analyte concentrations with the normalized reference correlation of FIG. 4E in comparison to when the underlying currents from the measurement device are transformed by the conventional reference correlation of FIG. 4A.

Figure 4F:
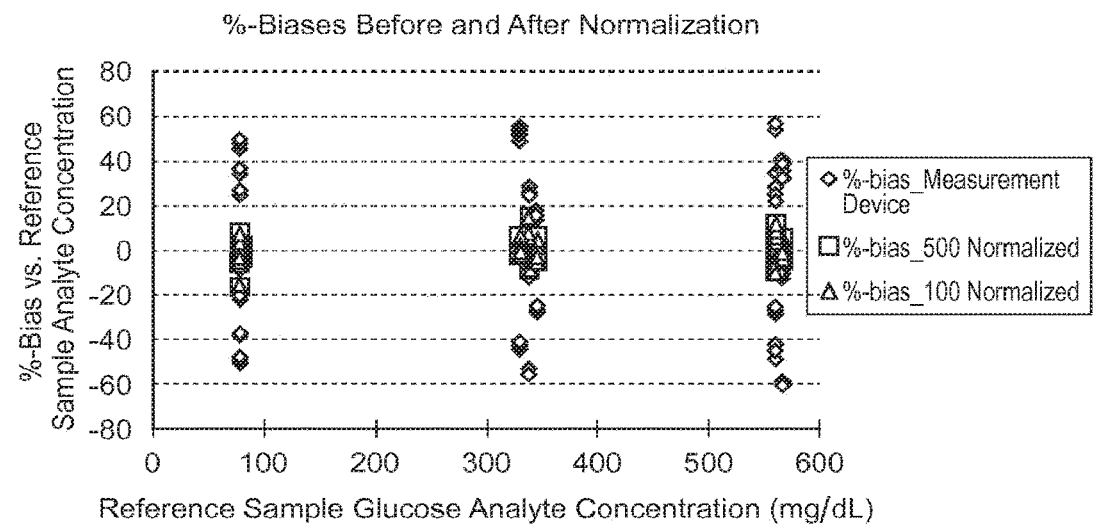
FIG. 4F plots the %-bias attributable to the different temperatures (6.0° C., 10.9° C., 15.9° C., 22.0° C., 30.4° C., 35.1° C., and 40.0° C.) before and after normalization.

FIG. 4F plots the %-bias of the determined glucose concentrations attributable to the different temperatures (6.0° C., 10.9° C., 15.9° C., 22.0° C., 30.4° C., 35.1° C., and 40.0° C.) before and after normalization. The measured currents showed a %-bias spread of approximately ±60 when transformed by the conventional reference correlation, while the normalized currents showed a %-bias spread of approximately ±20. Thus, an approximate 3× reduction in %-bias would be expected for sample analyte concentrations determined with a biosensor system including a measurement device including calibration information in accord with the present method in comparison to sample analyte concentrations determined with a measurement device including calibration information provided by a conventional method lacking normalization reduction of the temperature stimulus.

Once the effect of temperature is reduced, the effect of a second extraneous stimulus, such as sample hematocrit also may be substantially reduced using a two-step normalization process, thus the combination of FIG. 1A and FIG. 1B. In this type of glucose system, the working and counter electrodes provide the primary output signal while a temperature sensor preferably provides a secondary output signal and a hematocrit electrode preferably provides an additional secondary output signal. The secondary output signals responsive to temperature and hematocrit may arise in other ways, as previously discussed. The step-wise normalization by temperature and then by sample hematocrit was generally performed by normalizing the output currents from the measurement device at multiple temperatures (as described above) and then normalizing the resulting temperature normalized output signal currents for multiple Hct sample concentrations using a hematocrit normalization relationship.

An example of the calibration method 102 for determining calibration information with a reduced secondary extraneous stimulus effect for hematocrit on the primary output signal from an electrochemical glucose analysis system is shown in FIGS. 5A-5I. In this example, the sample analyte is glucose (the primary stimulus) and the sample analyte concentration is the glucose concentration in the sample of blood. Hematocrit concentration in the blood sample is the second extraneous stimulus in addition to the first extraneous stimulus, temperature. This method is represented with the plots in FIG. 5A through FIG. 5I. The numerical values calculated throughout FIGS. 5A-5I would be different for a different analysis system or even a different glucose analysis system.

Figure 5A:
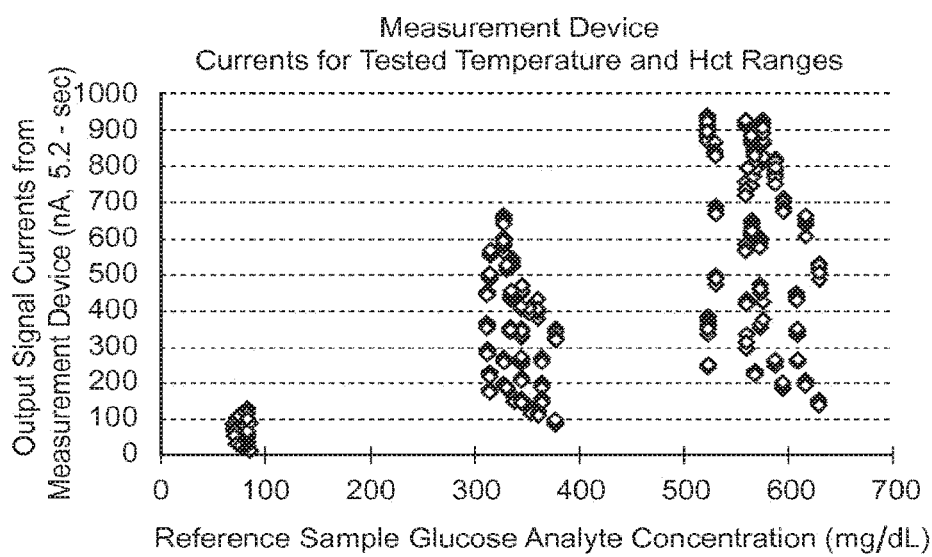
FIG. 5A shows the output signal currents from the measurement device for reference samples including known glucose concentrations for the tested temperatures (6.0° C., 10.9° C., 15.9° C., 22.0° C., 30.4° C., 35.1° C., and 40.0° C.) and for the tested Hct reference sample concentrations (0%, 20%, 40%, 55%, 70%).

FIG. 5A shows the output signal currents from the measurement device for reference samples including known glucose concentrations for the tested temperatures (6.0° C., 10.9° C., 15.9° C., 22.0° C., 30.4° C., 35.1° C., and 40.0° C.) and for the tested Hct reference sample concentrations (0%, 20%, 40%, 55%, 70%). The secondary output signals obtained from a hematocrit electrode were used to obtain the Hct responsive output currents from the reference samples having known hematocrit concentrations. As expected, the currents determined by the measurement device from reference samples including ~80 mg/dL glucose analyte concentration were closely grouped around ~75 nA, while the currents determined by the measurement device from reference samples including ~320 mg/dL and ~580 mg/dL glucose analyte concentrations were widely spaced.

Figure 5B:
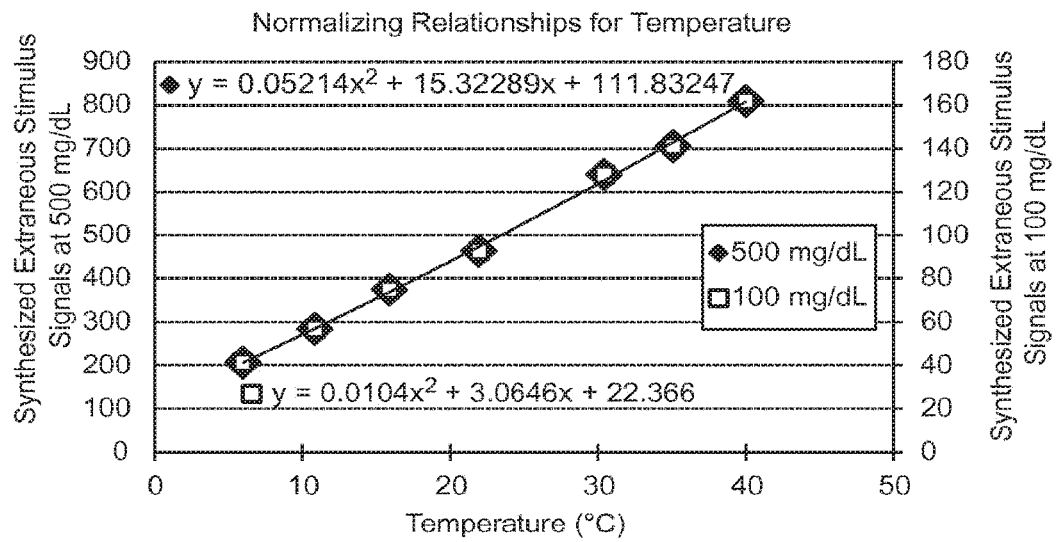
FIG. 5B represents the temperature normalizing relationships at 40% Hct and at two separate single glucose concentrations of 100 and 500 mg/dL in blood sample, and is the same as previously represented in FIG. 4C, as the same temperature stimulus reduction is being performed.

FIG. 5B represents the temperature normalizing relationships at 40% Hct and at two separate single glucose concentrations of 100 and 500 mg/dL in blood sample, and is the same as previously represented in FIG. 4C, as the same temperature stimulus reduction is being performed. Temperature normalization was the first step taken in this example to reduce the effect of extraneous stimulus from temperature, as the same temperature stimulus reduction was performed. From FIG. 5B, normalized analyte responsive output signals with a reduction in the effect of the temperature stimulus were determined as previously described.

Figure 5C:
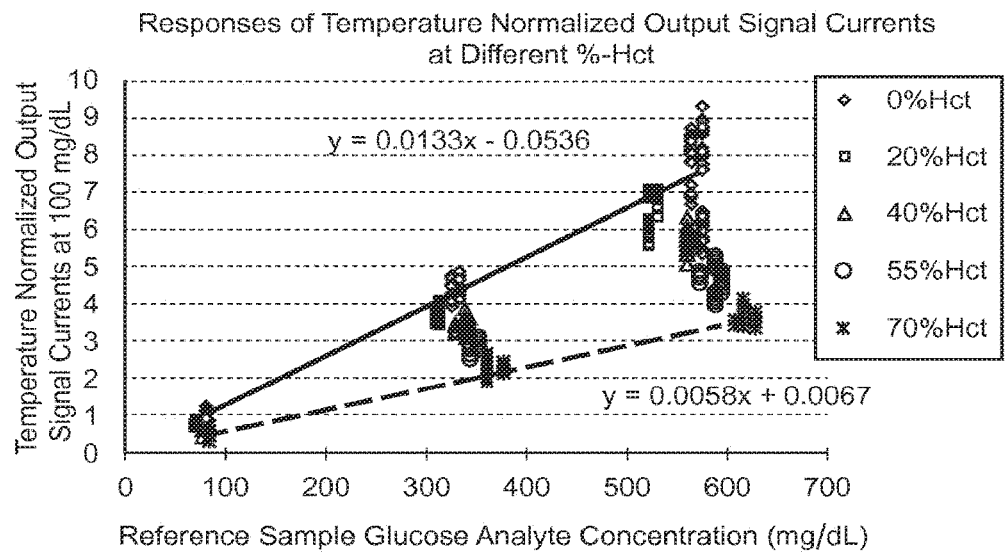
FIG. 5C plots the temperature normalized analyte responsive output signal values from FIG. 5A versus reference sample analyte concentration for glucose at the Hct reference sample concentrations tested in this example.
Figure 5D:
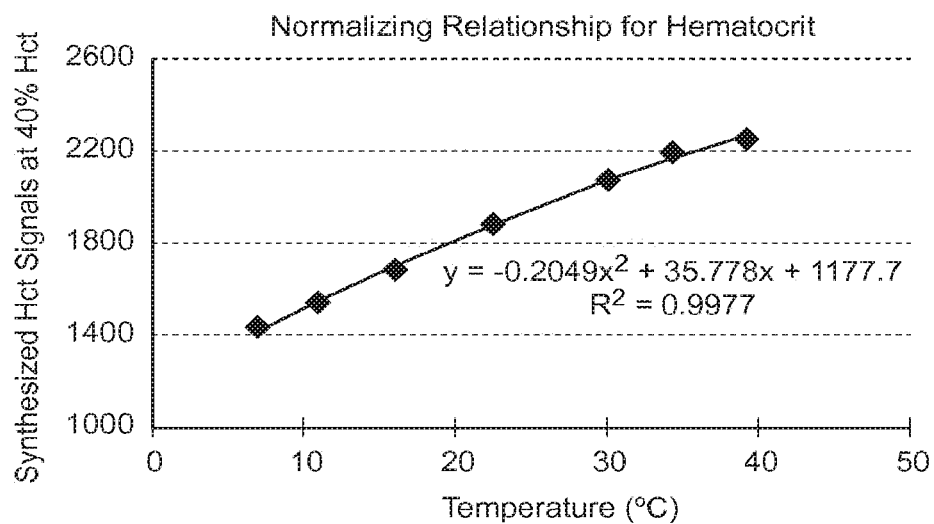
FIG. 5D plots the synthesized signals determined from the secondary output signal responsive to the hematocrit concentration of the sample verses temperature for reference samples including a 40% hematocrit concentration.
Figure 5E:
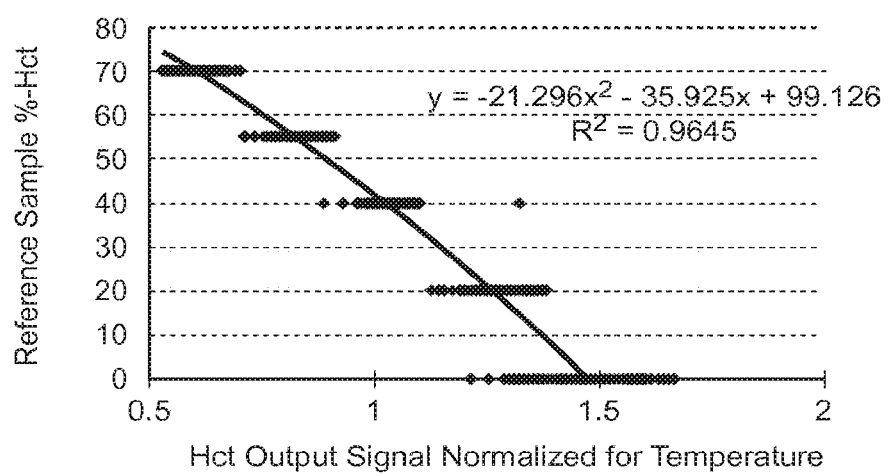
FIG. 5E shows the temperature normalized reference correlation for Hct where reference sample % Hct concentrations were plotted against the temperature normalized Hct electrode output currents.
Figure 5F:
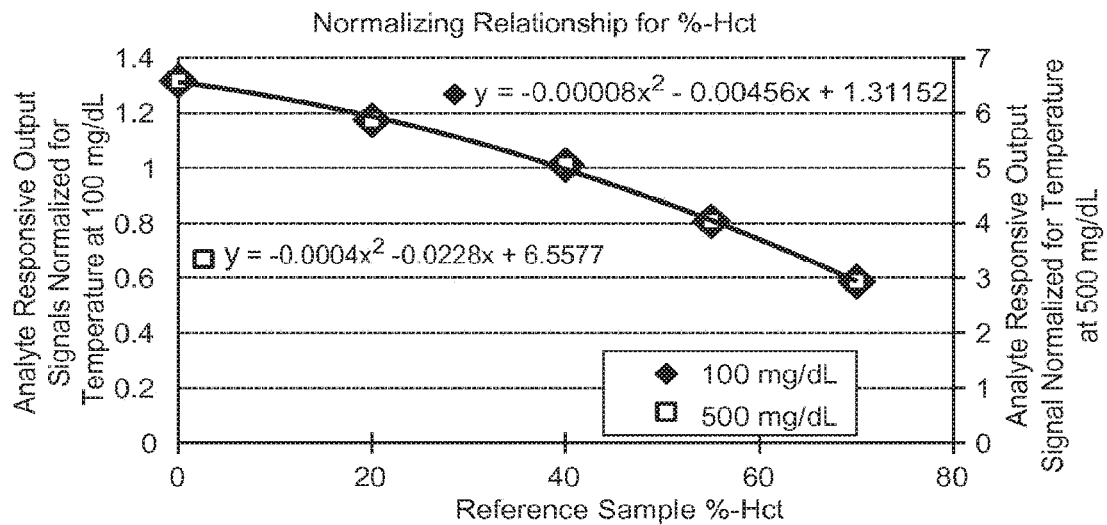
FIG. 5F represents the second normalizing relationship determined between the resulting temperature normalized analyte responsive output signals and the reference sample 10-Hct values—the second extraneous stimulus.
Figure 5G:
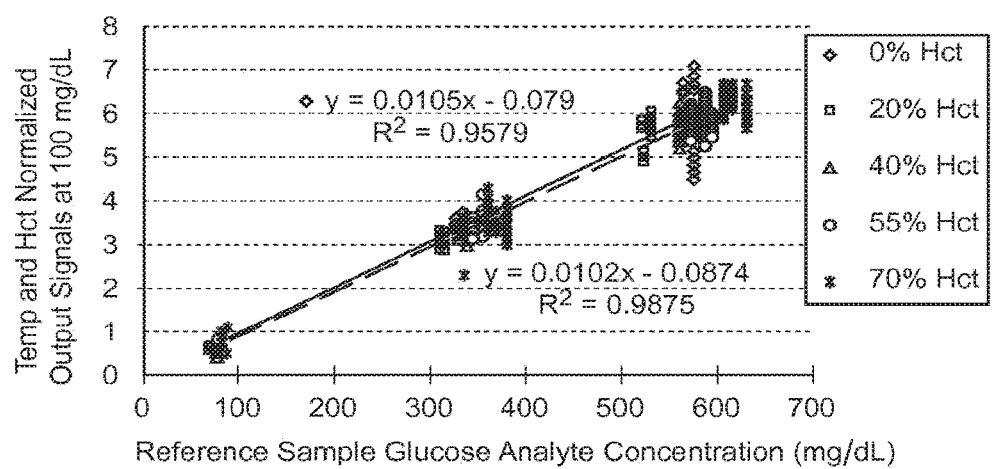
FIG. 5G graphically represents the reduction in error introduced by the extraneous stimulus of hematocrit as represented in FIG. 5C provided through the use of the temperature and Hct normalized analyte responsive output signal values at the selected glucose concentration of 100 mg/dL.
Figure 5H:
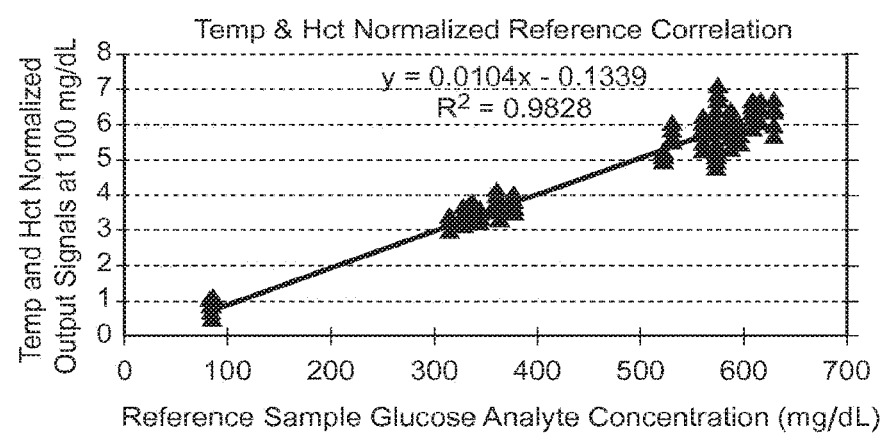
FIG. 5H provides an example of the determination of a normalized reference correlation from combining the temperature and hematocrit normalized analyte responsive output signal values of FIG. 5G.

FIG. 5C plots the temperature normalized analyte responsive output signal values from FIG. 5A versus reference sample analyte concentration for glucose at the Hct reference sample concentrations tested in this example. As expected, significant spread in the normalized currents is observed at higher glucose concentrations for the different Hct concentrations, even though the underlying sample analyte concentration is the same. FIG. 5C may be thought of as being similar to FIG. 4B, but showing the effect of the second extraneous stimulus, hematocrit as opposed to temperature.

Temperature as an error parameter or an extraneous stimulus is preferably measured concurrently with the primary stimulus and its value is independent of other factors. The hematocrit concentration in the blood samples is provided along with the glucose concentration, but the hematocrit responsive secondary output signals are temperature-dependent. Therefore, temperature is also an extraneous stimulus for the Hct responsive output signals and the effect of temperature is preferably reduced by normalization. The procedure involved is first to construct the Hct responsive currents plot against the temperature at a single selected Hct concentration. Then, a Hct normalized calibration curve is determined that provides the calculated %-Hct values from the temperature normalized Hct output signals for later use.

Synthesized Hct output signal values were generated similarly as previously described for A1c and glucose with regard to FIG. 2C and FIG. 4B, respectively. In this determination, which is not shown in a figure, the current recorded from the Hct electrode for the reference samples at each reference sample hematocrit concentration was plotted on the vertical y-axis while the known reference sample hematocrit concentrations were plotted on the horizontal X-axis. A regression line was plotted for each temperature (6.0° C., 10.9° C., 15.9° C., 22.0° C., 30.4° C., 35.1° C., and 40.0° C.) and a synthesized Hct output signal value was determined at a 40% sample hematocrit concentration for each temperature.

FIG. 5D plots the synthesized signals determined from the secondary output signal responsive to the hematocrit concentration of the sample verses temperature for reference samples including a 40% hematocrit concentration. From the above operation, seven pairs of the synthesized Hct output signals from a single selected Hct concentration of 40% and the temperatures, at which the reference samples were analyzed, were obtained and plotted. A regression technique, in this instance polynomial, was then used to determine a specific normalizing relationship for Hct as shown in the figure, but having the general form $NV_{Hct}=(b_2*T^2+b_1*T+b_0$, where $b_2$, $b_1$ and $b_0$ are the coefficients of the $2^{nd}$ order polynomial normalization function from curve-fitting and T is the temperature). A Hct normalizing value was determined, and normalized Hct electrode currents were determined with the general relationship $Ni\_{Hct}=i\_{Hct}/NV_{Hct}$, where $Ni\_{Hct}$ are the temperature normalized Hct electrode currents, $i\_{Hct}$ are the Hct responsive currents from the Hct electrode, and $NV_{Hct}$ is the Hct normalizing value.

FIG. 5E shows the temperature normalized reference correlation for Hct where reference sample % Hct concentrations were plotted against the temperature normalized Hct electrode output currents. Other interferents may be similarly treated if the biosensor system provides a secondary output signal responsive to the interferent.

FIG. 5F represents the second normalizing relationship determined between the resulting temperature normalized analyte responsive output signals and the reference sample %-Hct values—the second extraneous stimulus. FIG. 5F established the correlation between the temperature normalized output signals and the sample %-Hct concentrations. That is, at the single selected glucose concentration of either 100 or 500 mg/dL, the temperature normalized output signals are substantively responsive to the Hct concentration, the second extraneous stimulus.

A regression technique, in this case polynomial ($c_2*Hct^2+c_1*Hct+c_0$, where $c_2$, $c_1$ and $c_0$ are the coefficients of the $2^{nd}$ order polynomial normalization function from curve-fitting and Hct is the second quantified extraneous stimulus value for Hct), was then used to determine the normalizing relationship between the synthesized second extraneous stimulus responsive output signals at a single selected sample analyte concentration and the quantified second extraneous stimulus values (reference sample hematocrit concentrations of 0%, 20%, 40%, 55%, and 70%. The specific normalization relationship for the 100 and 500 mg/dL glucose analysis data from this example is shown in FIG. 5F as $y=-0.00008X^2-0.00456X+1.31152$ (100 mg/dL) and $y=-0.0004X^2-0.0228X+6.5577$ (500 mg/dL), thus showing the specific $2^{nd}$ order polynomial coefficients for this example, where Y is the calculated synthesized second extraneous stimulus responsive output signal responsive to the second extraneous stimulus (Hct) at a single selected analyte concentration, and X is the quantified second extraneous stimulus values. A different analysis would have different coefficients. When a value of X (the quantified second extraneous stimulus signal value) is entered into the $2^{nd}$ order polynomial, a value of Y is generated through this normalizing relationship, which is the normalizing value (NV).

Second normalized analyte responsive output signals 167 were then determined from the normalizing value at 100 mg/dL. Thus, the temperature normalized output signals from the vertical Y-axis of FIG. 5C were then converted to second normalized primary signal values using the normalization relationship of FIG. 5F with their corresponding normalizing values. The determination of the normalized analyte responsive signals from the normalizing value may be represented by the relationship $Ni_G=i_{measured}/NV_{TempHct}$, where $Ni_G$ are the temperature and hematocrit normalized analyte responsive signals, $i_{measured}$ are the glucose responsive currents from the measurement device, and $NV_{TempHct}$ is the normalizing value determined from temperature and hematocrit normalization.

FIG. 5G graphically represents the reduction in error introduced by the extraneous stimulus of hematocrit as represented in FIG. 5C provided through the use of the temperature and Hct normalized analyte responsive output signal values at the selected glucose concentration of 100 mg/dL. Thus, this figure may be thought of similarly as to FIG. 4C; however, in this example, both temperature and hematocrit normalized currents are used. Regression equations are shown for the lower (0%) and upper (70%) limit Hct concentrations. In relation to FIG. 5C, the divergence between the upper and lower Hct limits has been reduced from approximately 4 normalized output signal units (FIG. 5C) to approximately 0.25 output signal units (FIG. 5G) at ~600 mg/dL, an approximate 93% reduction (4−0.25/4*100) in divergence between the regression lines.

FIG. 5H provides an example of the determination of a normalized reference correlation from combining the temperature and hematocrit normalized analyte responsive output signal values of FIG. 5G. The temperature and hematocrit normalized signals were plotted on the vertical Y-axis versus the reference sample analyte concentrations for glucose and curve-fitted by a regression technique to provide the normalized reference correlation. A regression technique, in this case linear (Y=Slope*X+Int), was used to determine the normalized reference correlation, where during the analysis 200 Y is a normalized primary output signal value determined by the measurement device and X is the determined analyte concentration of the sample.

The specific normalized reference correlation for the glucose analysis data from this example is shown in FIG. 5H as Y=0.0104X−0.1339, thus showing the specific linear coefficients for this example. A different analysis would have different coefficients. Also shown in FIG. 5H is the $R^2=0.9828$, showing the excellent agreement between the normalized primary output signals and the reference sample analyte concentrations for glucose. Thus, the normalized reference correlation relates the normalized output signals and the sample analyte concentration. When a normalized output signal is input into the normalized reference correlation, a sample analyte concentration is generated. FIG. 5H may be thought of as being similar to FIG. 4E except incorporating both temperature and Hct normalization into the calibration information.

For the hematocrit concentrations provided from the blood samples (0%, 20%, 40%, 55%, and 70%), the slopes of the reference correlations with temperature and temperature/hematocrit normalizations are tabulated in Table 5, where Slope/T is the slope from the temperature normalized reference correlation and Slope/T/H is the slope from the temperature and hematocrit normalized reference correlation.

TABLE 5

Summary of Normalization for Temperature and Hematocrit Stimuli

| % Hct | Slope/T FIG. 4C | Slope/T/H FIG. 4G |
|---|---|---|
| 0 | 0.0133 | 0.0105 |
| 20 | 0.0126 | 0.0107 |
| 40 | 0.0105 | 0.0105 |
| 55 | 0.0082 | 0.0101 |
| 70 | 0.0058 | 0.0102 |
| Mean slope | 0.0101 | 0.0104 |
| SD, slope | 0.0031 | 0.0002 |
| % CV | 30.7 | 2.3 |

The improvement in measurement performance may be better appreciated by looking at the mean response slopes and the %-CV of the slopes for temperature normalization alone and after normalization for both temperature and hematocrit. In this example, the %-CV of the response slopes determined with a temperature normalized reference correlation was 30.7%. In contrast, the %-CV of the response slopes determined with the described temperature and hematocrit normalized reference correlation was reduced to 2.3%, an approximate 92% reduction (30.7−2.3/30.7*100) in %-CV providing a substantial increase in measurement performance to the biosensor system.

Figure 5I:
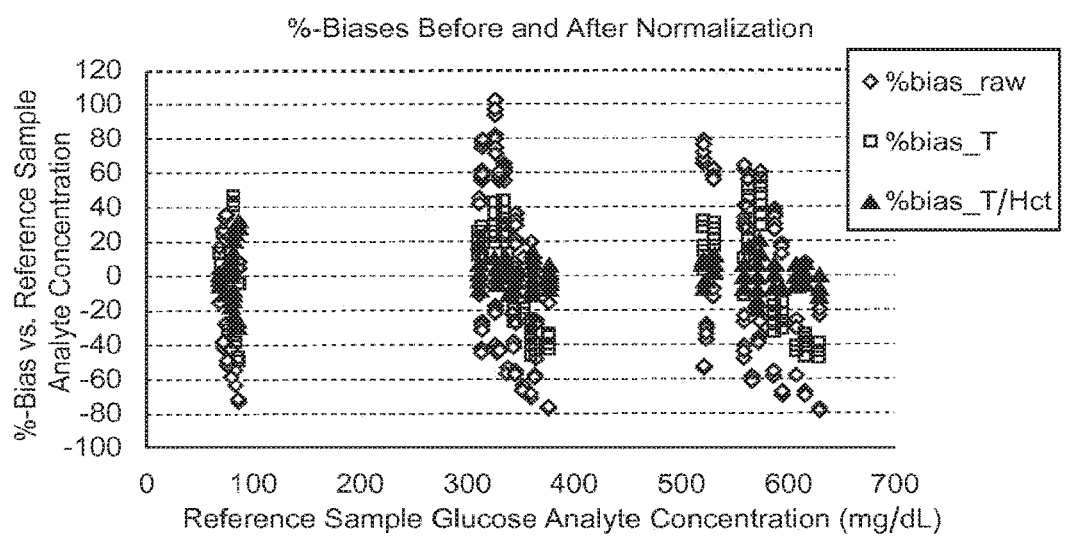
FIG. 5I graphically represents the %-bias of the analyte concentrations that were determined by a measurement device using a conventional reference correlation (% bias_raw), a temperature normalized reference correlation (% bias_T), and a temperature and Hct normalized reference correlation (% bias_T/Hct).

FIG. 5I graphically represents the %-bias of the analyte (glucose) concentrations determined by the measurement device of a biosensor system using a conventional reference correlation (% bias_raw), a temperature normalized reference correlation (% bias_T), and a temperature and Hct normalized reference correlation (% bias_T/Hct). The figure establishes that the output currents including the temperature and hematocrit stimuli in combination show a %-bias of nearly ±100% when directly transformed with a conventional reference correlation into sample analyte concentrations. Removal of the temperature stimulus from the calibration information allows the measurement device to determine analyte concentrations with a %-bias of approximately ±50%, while further removal of the Hct stimulus reduces the %-bias to approximately ±30%. Thus, an approximately 70% reduction in %-bias was observed with the described normalized calibration information in relation to conventional calibration information. This is a substantial improvement in relation to conventional systems with regard to the measurement performance the biosensor system may provide from the calibration information without additional compensation.

Figure 6:
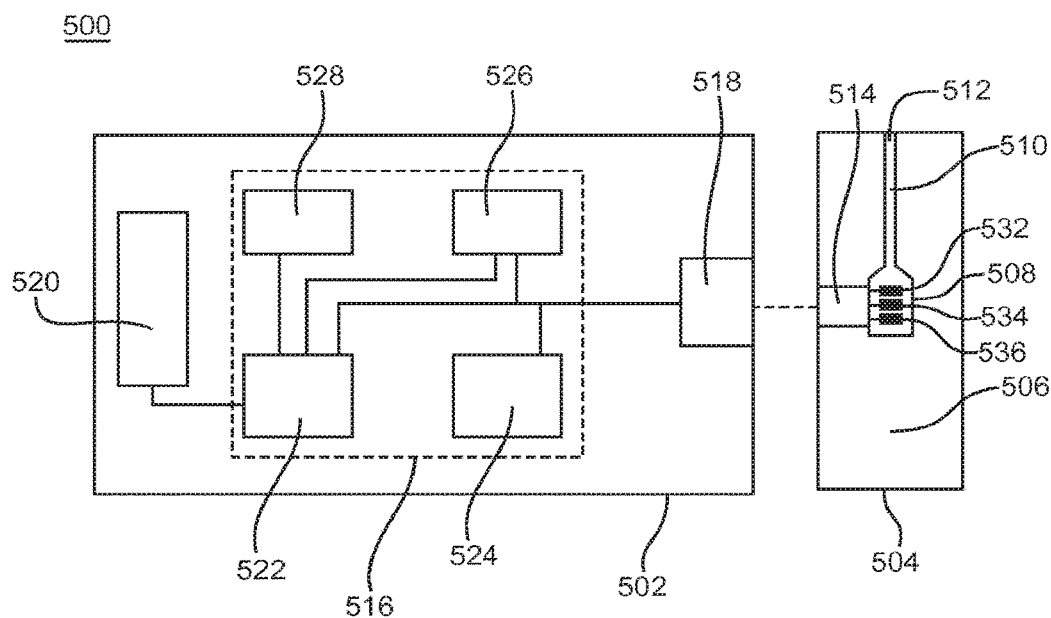
FIG. 6 depicts a schematic representation of a biosensor system that determines an analyte concentration in a sample of a biological fluid.

FIG. 6 depicts a schematic representation of a biosensor system 500 that determines an analyte concentration in a sample of a biological fluid. Biosensor system 500 includes a measurement device 502 and a test sensor 504. The measurement device 502 may be implemented in an analytical instrument, including a bench-top device, a portable or hand-held device, or the like. Preferably the measurement device 502 is implemented in a hand-held device. The measurement device 502 and the test sensor 504 may be adapted to implement an electrochemical sensor system, an optical sensor system, a combination thereof, or the like.

The biosensor system 500 determines the analyte concentration of the sample using the calibration information developed in accord with the previously described normalization techniques and stored in the measurement device 502. The calibration information from one or both of the calibration methods 100 and 102 may be stored in the measurement device 502. The calibration information includes one or more normalizing relationships and one or more normalized reference correlations. One or both calibration methods 100 and 102 may be stored in the measurement device 502 so the normalized calibration information may be determined by the measurement device 502. The analysis method 200 may be stored in the measurement device for implementation by the biosensor system 500. The method of measurement device calibration may improve the measurement performance of the biosensor system 500 in determining the analyte concentration of the sample. The biosensor system 500 may be utilized to determine analyte concentrations, including those of glucose, A1c, uric acid, lactate, cholesterol, bilirubin, and the like. While a particular configuration is shown, the biosensor system 500 may have other configurations, including those with additional components.

The test sensor 504 has a base 506 that forms a reservoir 508 and a channel 510 with an opening 512. The reservoir 508 and the channel 510 may be covered by a lid with a vent. The reservoir 508 defines a partially-enclosed volume. The reservoir 508 may contain a composition that assists in retaining a liquid sample such as water-swellable polymers or porous polymer matrices. Reagents may be deposited in the reservoir 508 and/or the channel 510. The reagents may include one or more enzymes, binders, mediators, and like species. The reagents may include a chemical indicator for an optical system. The test sensor 504 has a sample interface 514 adjacent to the reservoir 508. The test sensor 504 may have other configurations.

In an optical sensor system, the sample interface 514 has an optical portal or aperture for viewing the sample. The optical portal may be covered by an essentially transparent material. The sample interface 514 may have optical portals on opposite sides of the reservoir 508.

In an electrochemical system, the sample interface 514 has conductors connected to a working electrode 532 and a counter electrode 534 from which the analytic output signal may be measured. The sample interface 514 also may include conductors connected to one or more additional electrodes 536 from which secondary output signals may be measured. The electrodes may be substantially in the same plane or in more than one plane. The electrodes may be disposed on a surface of the base 506 that forms the reservoir 508. The electrodes may extend or project into the reservoir 508. A dielectric layer may partially cover the conductors and/or the electrodes. The sample interface 514 may have other electrodes and conductors.

The measurement device 502 includes electrical circuitry 516 connected to a sensor interface 518 and an optional display 520. The electrical circuitry 516 includes a processor 522 connected to a signal generator 524, an optional temperature sensor 526, and a storage medium 528.

The signal generator 524 is capable of providing an electrical input signal to the sensor interface 518 in response to the processor 522. In optical systems, the electrical input signal may be used to operate or control the detector and light source in the sensor interface 518. In electrochemical systems, the electrical input signal may be transmitted by the sensor interface 518 to the sample interface 514 to apply the electrical input signal to the sample of the biological fluid. The electrical input signal may be a potential or current and may be constant, variable, or a combination thereof, such as when an AC signal is applied with a DC signal offset. The electrical input signal may be applied continuously or as multiple excitations, sequences, or cycles. The signal generator 524 also may be capable of recording an output signal from the sensor interface as a generator-recorder.

The optional temperature sensor 526 is capable of determining the ambient temperature of the measurement device 502. The temperature of the sample may be estimated from the ambient temperature of the measurement device 502, calculated from the output signal, or presumed to be the same or similar to the ambient temperature of the measurement device 502. The temperature may be measured using a thermister, thermometer, or other temperature sensing device. Other techniques may be used to determine the sample temperature.

The storage medium 528 may be a magnetic, optical, or semiconductor memory, another storage device, or the like. The storage medium 528 may be a fixed memory device, a removable memory device, such as a memory card, remotely accessed, or the like.

The processor 522 is capable of implementing the analyte analysis method using computer readable software code and the calibration information stored in the storage medium 528. The processor 522 may start the analyte analysis in response to the presence of the test sensor 504 at the sensor interface 518, the application of a sample to the test sensor 504, in response to user input, or the like. The processor 522 is capable of directing the signal generator 524 to provide the electrical input signal to the sensor interface 518. The processor 522 is capable of receiving the sample temperature from the temperature sensor 526. The processor 522 is capable of receiving the output signals from the sensor interface 518.

In electrochemical systems, the analyte responsive primary output signal is generated from the working and counter electrodes 532, 534 in response to the reaction of the analyte in the sample. Secondary output signals also may be generated from additional electrodes 536. In optical systems, the detector or detectors of the sensor interface 518 receive the primary and any secondary output signals. The output signals may be generated using an optical system, an electrochemical system, or the like. The processor 522 is capable of determining analyte concentrations from output signals using the calibration information stored in the storage medium 528. The results of the analyte analysis may be output to the display 520, a remote receiver (not shown), and/or may be stored in the storage medium 528.

The calibration information relating reference sample analyte concentrations and output signals from the measurement device 502 may be represented graphically, mathematically, a combination thereof, or the like. The calibration information is preferably represented as correlation equations, which may be represented by a program number (PNA) table, another look-up table, or the like that is stored in the storage medium 528.

Instructions regarding implementation of the analyte analysis also may be provided by the computer readable software code stored in the storage medium 528. The code may be object code or any other code describing or controlling the described functionality. The data from the analyte analysis may be subjected to one or more data treatments, including the determination of decay rates, K constants, ratios, functions, and the like in the processor 522.

In electrochemical systems, the sensor interface 518 has contacts that connect or electrically communicate with the conductors in the sample interface 514 of the test sensor 504. The sensor interface 518 is capable of transmitting the electrical input signal from the signal generator 524 through the contacts to the connectors in the sample interface 514. The sensor interface 518 also is capable of transmitting the output signal from the sample through the contacts to the processor 522 and/or signal generator 524.

In light-absorption and light-generated optical systems, the sensor interface 518 includes a detector that collects and measures light. The detector receives light from the test sensor 504 through the optical portal in the sample interface 514. In a light-absorption optical system, the sensor interface 518 also includes a light source such as a laser, a light emitting diode, or the like. The incident beam may have a wavelength selected for absorption by the reaction product. The sensor interface 518 directs an incident beam from the light source through the optical portal in the sample interface 514. The detector may be positioned at an angle such as 45° to the optical portal to receive the light reflected back from the sample. The detector may be positioned adjacent to an optical portal on the other side of the sample from the light source to receive light transmitted through the sample. The detector may be positioned in another location to receive reflected and/or transmitted light.

The optional display 520 may be analog or digital. The display 520 may include a LCD, a LED, an OLED, a vacuum fluorescent display, or other display adapted to show a numerical reading. Other display technologies may be used. The display 520 electrically communicates with the processor 522. The display 520 may be separate from the measurement device 502, such as when in wireless communication with the processor 522. Alternatively, the display 520 may be removed from the measurement device 502, such as when the measurement device 502 electrically communicates with a remote computing device, medication dosing pump, and the like.

In use, a liquid sample for analysis is transferred into the reservoir 508 by introducing the liquid to the opening 512. The liquid sample flows through the channel 510, filling the reservoir 508 while expelling the previously contained air. The liquid sample chemically reacts with the reagents deposited in the channel 510 and/or reservoir 508.

The test sensor 502 is disposed in relation to the measurement device 502, such that the sample interface 514 is in electrical and/or optical communication with the sensor interface 518. Electrical communication includes the transfer of input and/or output signals between contacts in the sensor interface 518 and conductors in the sample interface 514. Optical communication includes the transfer of light between an optical portal in the sample interface 514 and a detector in the sensor interface 518. Optical communication also includes the transfer of light between an optical portal in the sample interface 514 and a light source in the sensor interface 518.

The processor 522 is capable of directing the signal generator 524 to provide an input signal to the sensor interface 518 of the test sensor 504. In an optical system, the sensor interface 518 is capable of operating the detector and light source in response to the input signal. In an electrochemical system, the sensor interface 518 is capable of providing the input signal to the sample through the sample interface 514. The test sensor 504 is capable of generating one or more output signals in response to the input signal. The processor 522 is capable of receiving the output signals generated in response to the redox reaction of the analyte in the sample as previously discussed.

The processor 522 is capable of transforming the output signal using the analysis method and the calibration information stored in the storage medium 528 to determine an initial analyte concentration of the sample. The processor 522 may then report this initial analyte concentration as the final analyte concentration of the sample. Alternatively, the processor 522 may further process this initial analyte concentration of the sample using a compensation system. More than one compensation and/or other functions also may be implemented by the processor 522.

To provide a clear and more consistent understanding of the specification and claims of this application, the following definitions are provided.

"Average" or "Averaged" or "Averaging" includes the combination of two or more variables to form an average variable. A variable may be a numerical value, an algebraic or scientific expression, or the like. For example, averaging may be performed by adding the variables and dividing the sum by the number of variables; such as in the equation $AVG=(a+b+c)/3$, where AVG is the average variable and a, b, and c are the variables. In another example, averaging includes modifying each variable by an averaging coefficient and then adding the modified variables to form a weighted average; such as in the equation $W_{AVG}=0.2*a+0.4*b+0.4*c$, where $W_{AVG}$ is the weighted average, 0.2, 0.4 and 0.4 are the averaging coefficients, and a, b, and c are the variables. The averaging coefficients are numbers between 0 and 1; and if added, will provide a sum of 1 or substantially 1. Other averaging methods may be used.

"Measurable species" addresses a species the biosensor system is designed to determine the presence and/or concentration of in the sample and may be the analyte of interest or a mediator whose concentration in the sample is responsive to that of the analyte of interest.

While various embodiments of the invention have been described, it will be apparent to those of ordinary skill in the art that other embodiments and implementations are possible within the scope of the invention.

What is claimed is:

1. A method for determining an analyte concentration in a sample using a sensor, comprising:
    generating at least one output signal from a sample;
    measuring at least one analyte responsive output signal value from the at least one output signal, where the at least one analyte responsive output signal value is affected by an error in the output signal from at least one extraneous stimulus;
    measuring at least one extraneous stimulus responsive output signal value from the sample, the at least one extraneous stimulus responsive output signal value being independent of the analyte responsive output signal value;
    determining at least one quantified extraneous stimulus value in response to the at least one extraneous stimulus output signal value;
    determining at least one normalizing value from at least one normalizing relationship that is included in normalized calibration information relating the output signal to previously determined reference sample analyte concentrations, the normalizing relationship being a relationship determined between the analyte responsive output signal value and the quantified extraneous stimulus value;
    determining at least one normalized analyte responsive output signal value in response to the at least one analyte responsive output signal value and the at least one normalizing value; and
    determining at least one analyte concentration in the sample in response to at least one normalized reference correlation and the at least one normalized analyte responsive output signal.

2. The method of claim 1, wherein the determining at least one normalizing value comprises inputting the at least one analyte responsive output signal value and the at least one quantified extraneous stimulus value into the at least one normalizing relationship.

3. The method of claim 1, wherein the determining at least one normalized analyte responsive output signal value includes dividing the at least one analyte responsive output signal value by the at least one normalizing value.

4. The method of claim 3, wherein one analyte responsive output signal value is used to determine one normalized analyte responsive output signal value.

5. The method of claim 1, wherein the determining at least one analyte concentration includes the at least one normalized reference correlation transforming the at least one normalized analyte responsive output signal value into the at least one analyte concentration.

6. The method of claim 1, further comprising determining an average analyte concentration of the sample from at least two analyte concentrations.

7. The method of claim 1, wherein the determining at least one normalizing value includes inputting the at least one analyte responsive output signal value and the at least one quantified extraneous stimulus value into the at least one normalizing relationship.

8. The method of claim 1, further comprising:
    determining the normalizing relationship between at least two analyte responsive output signals and at least two quantified extraneous stimulus values;
    determining the at least two quantified extraneous stimulus values from the at least one extraneous stimulus responsive output signal;
    measuring at least one extraneous stimulus responsive output signal from at least one reference sample; and
    determining a reference correlation between a reference sample analyte concentration of the at least one reference sample and at least two analyte responsive output signals;
    determining the at least one normalized reference correlation between at least two normalized analyte responsive output signals and the reference sample analyte concentration; and
    determining the at least two normalized analyte responsive output signals from the at least two analyte responsive output signals and the normalizing value.

9. The method of claim 8,
    wherein determining the normalizing relationship includes applying a normalizing relationship regression technique to the at least two analyte responsive output signals and the at least two quantified extraneous stimulus values at a single selected analyte concentration; and
    wherein determining the at least one normalized reference correlation includes applying a normalized reference correlation regression technique to the at least two normalized analyte responsive output signals and the at least one reference sample analyte concentration.

10. The method of claim 8, further comprising:
    determining at least two second quantified extraneous stimulus values from the at least one extraneous stimulus responsive output signal;
    determining a second normalizing relationship between the at least two normalized analyte responsive output signals and the at least two second quantified extraneous stimulus values;

determining at least two second normalized analyte responsive output signals from the at least two normalized analyte responsive output signals and a second normalizing value; and determining a second normalized reference correlation between the at least two second normalized analyte responsive output signals and the at least one reference sample analyte concentration.

11. The method of claim 10, wherein the determining of a second normalizing relationship includes applying a second normalizing relationship regression technique to the at least two normalized analyte responsive output signals and the at least two second quantified extraneous stimulus values at a single selected analyte concentration; and wherein determining a second normalized reference correlation includes applying a second normalized reference correlation regression technique to the at least two second normalized analyte responsive output signals and the at least one reference sample analyte concentration.

12. The method of claim 1, wherein the at least one extraneous stimulus includes at least one of a physical characteristic, an environmental aspect, and a manufacturing variation.

13. The method of claim 1, wherein the at least one analyte concentration includes at least one of glycated hemoglobin and glucose;

wherein the sample includes blood; and wherein the at least one extraneous stimulus includes at least one of temperature, total hemoglobin, and hematocrit.

14. A biosensor system for determining an analyte concentration in a sample, comprising:

a test sensor having a sample interface adjacent to a reservoir formed by a base, where the test sensor is capable of generating at least one output signal from a sample; and a measurement device having a processor connected to a sensor interface, the sensor interface having Electrical communication with the sample interface, and the processor having Electrical communication with a storage medium;

where the processor is capable of measuring at least one analyte responsive output signal value from the at least one output signal, where the at least one analyte responsive output signal value is affected by at least one extraneous stimulus;

where the processor is capable of measuring at least one extraneous stimulus responsive output signal value from the sample, the at least one extraneous stimulus responsive output signal value being independent of the analyte responsive output signal value;

where the processor is capable of determining at least one quantified extraneous stimulus value in response to the at least one extraneous stimulus output signal value;

where the processor is capable of determining at least one normalizing value from at least one normalizing relationship that is included in normalized calibration information relating the output signal to previously determined reference sample analyte concentrations, the normalizing relationship being a relationship determined between the analyte responsive output signal value and the quantified extraneous stimulus value;

where the processor is capable of determining at least one normalized analyte responsive output signal value in response to the at least one analyte responsive output signal value and the at least one normalizing value; and where the processor is capable of determining at least one analyte concentration in the sample in response to at least one normalized reference correlation and the at least one normalized analyte responsive output signal.

15. The biosensor system of claim 14, wherein the at least one extraneous stimulus is at least one of a physical characteristic, an environmental aspect, and a manufacturing variation.

16. The biosensor system of claim 14, wherein the processor is capable of determining an average analyte concentration of the sample from at least two analyte concentrations.

17. The biosensor system of claim 14, wherein the at least one analyte concentration includes at least one of glycated hemoglobin and glucose, and where the sample comprises blood.

18. The biosensor system of claim 14, wherein the at least one extraneous stimulus is at least one of temperature, total hemoglobin, and hematocrit.

19. The biosensor system of claim 14, wherein the at least one normalizing relationship and the at least one normalized reference correlation are stored in the storage medium.

20. The biosensor system of claim 14, wherein the processor is capable of measuring at least two analyte responsive output signals;

wherein the processor is capable of determining a reference correlation between at least one reference sample analyte concentration and the at least two analyte responsive output signals;

wherein the processor is capable of measuring at least one extraneous stimulus responsive output signal from the sample;

wherein the processor is capable of determining at least two quantified extraneous stimulus values from the at least one extraneous stimulus responsive output signal;

wherein the processor is capable of determining the normalizing relationship between the at least two analyte responsive output signals and the at least two quantified extraneous stimulus values;

wherein the processor is capable of determining a normalizing value from the normalizing relationship and the at least two quantified extraneous stimulus values;

wherein the processor is capable of determining at least two normalized analyte responsive output signals from the at least two analyte responsive output signals and the normalizing value; and wherein the processor is capable of determining the normalized reference correlation between the at least two normalized analyte responsive output signals and the at least one reference sample analyte concentration.

* * * * *